US009421194B2

(12) United States Patent
Prud'homme et al.

(10) Patent No.: US 9,421,194 B2
(45) Date of Patent: Aug. 23, 2016

(54) LUNG TARGETING DUAL DRUG DELIVERY SYSTEM

(75) Inventors: Robert K. Prud'homme, Lawrenceville, NJ (US); Patrick J. Sinko, Annandale, NJ (US); Howard A. Stone, Princeton, NJ (US); Nathalie M. Pinkerton, Ottawa Hills, OH (US); Lei Shi, Shanghai (CN); Jiandi Wan, Lawrenceville, NJ (US); Sherif Ibrahim, Old Bridge, NJ (US); Dayuan Gao, East Brunswick, NJ (US)

(73) Assignees: Rutgers, The State University of New Jersey, New Brunswick, NJ (US); The Trustees of Princeton University, Princeton, NJ (US)

( * ) Notice: Subject to any disclaimer, the term of this patent is extended or adjusted under 35 U.S.C. 154(b) by 15 days.

(21) Appl. No.: 13/080,371

(22) Filed: Apr. 5, 2011

(65) Prior Publication Data
US 2011/0268803 A1 Nov. 3, 2011

Related U.S. Application Data

(60) Provisional application No. 61/320,941, filed on Apr. 5, 2010.

(51) Int. Cl.
*A61K 31/437* (2006.01)
*A61K 9/00* (2006.01)
*A61K 9/16* (2006.01)

(52) U.S. Cl.
CPC ............ *A61K 31/437* (2013.01); *A61K 9/0019* (2013.01); *A61K 9/1635* (2013.01); *A61K 9/1641* (2013.01); *A61K 9/1647* (2013.01)

(58) Field of Classification Search
CPC ... A61K 31/437; A61K 47/34; A61K 9/0019; A61K 9/1635; A61K 9/1641; A61K 9/1647; A61K 9/5138; A61K 9/5146; A61K 9/5192
See application file for complete search history.

(56) References Cited

U.S. PATENT DOCUMENTS

| 2005/0002975 A1* | 1/2005 | Cao ............................... 424/401 |
| 2008/0102114 A1* | 5/2008 | Koritala et al. ............... 424/456 |
| 2008/0260725 A1* | 10/2008 | Naik et al. .................. 424/130.1 |

OTHER PUBLICATIONS

Qiu et al. Biomaterials, 24, 2004, 11-18.*
Hasan et al., Int J Pharmaceutics, 344, 2007, 53-61.*
Akagi Y, Matsunaga T, Shibayama M, Chung U, Sakai T. Evaluation of Topological Defects in Tetra-PEG Gels. Macromolecules. Jan. 2010;43(1):488-493.
Akbulut M, Ginart P, Gindy ME, et al. Generic Method of Preparing Multifunctional Fluorescent Nanoparticles Using Flash NanoPrecipitation. Advanced Functional Materials. Mar. 2009;19(5):718-725.
Anna SL, Bontoux N, Stone HA. Formation of dispersions using "flow focusing" in microchannels. Applied Physics Letters. Jan. 2003;82(3):364-366.
Ansell SM, Johnstone SA, Tardi PG, et al. Modulating the therapeutic activity of nanoparticle delivered paclitaxel by manipulating the hydrophobicity of prodrug conjugates. Journal of Medicinal Chemistry. Jun. 2008;51(11):3288-3296.
Anseth KS, Bowman CN, BrannonPeppas L. Mechanical properties of hydrogels and their experimental determination. Biomaterials. Sep. 1996;17(17):1647-1657.
Aranda A, Pascual A. Nuclear Hormone Receptors and Gene Expression. Physiol. Rev. Jul. 1, 2001;81(3):1269-1304.
Beamish JA, Zhu JM, Kottke-Marchant K, Marchant RE. The effects of monoacrylated poly(ethylene glycol) on the properties of poly(ethylene glycol) diacrylate hydrogels used for tissue engineering. Journal of Biomedical Materials Research Part A. Feb. 2010;92A(2):441-450.
Benoit Gr, Cooney A, Giguere V, et al. International Union of Pharmacology. LXVI. Orphan Nuclear Receptors. Pharmacological Reviews. 2006;58(4):798-836.
Bjornstrom L, Sjoberg M. Estrogen receptor-dependent activation of AP-1 via non-genomic signalling. Nuclear Receptor. 2004;2(1):3.
Bryant SJ, Anseth KS, Lee DA, Bader DL. Crosslinking density influences the morphology of chondrocytes photoencapsulated in PEG hydrogels during the application of compressive strain. Journal of Orthopaedic Research. Sep. 2004;22(5):1143-1149.
Brzozowski AM, Pike ACW, Dauter Z, et al. Molecular basis of agonism and antagonism in the oestrogen receptor. Nature. 1997;389(6652):753-758.
Budijono SJ, Shan J, Yao N, et al. Synthesis of Stable Block-Copolymer-Protected NaYF4:Yb3+, Er3+ Up-Converting Phosphor Nanoparticles. Chemistry of Materials. 2009;22(2):311-318.
Busch BB, Stevens WC, Martin R, et al. Identification of a Selective Inverse Agonist for the Orphan Nuclear Receptor Estrogen-Related Receptor α±. Journal of Medicinal Chemistry. 2004;47(23):5593-5596.
Carroll NJ, Rathod SB, Derbins E, Mendez S, Weitz DA, Petsev DN. Droplet-based microfluidics for emulsion and solvent evaporation synthesis of monodisperse mesoporous silica microspheres. Langmuir. Feb. 2008;24(3):658-661.

(Continued)

Primary Examiner — Kyle Purdy
(74) Attorney, Agent, or Firm — Volpe and Koenig, P.C.

(57) ABSTRACT

The American Cancer Society estimated that in 2009, 1,479,350 new cancer cases would be diagnosed in the United States of which 219,440 would be lung and bronchus related. The standard treatments for NSCLC include surgery, chemotherapy, radiation, laser and photodynamic therapy, all with various success rates depending on the stage of the cancer. National Cancer Institute assesses, however, that results of standard treatment are generally poor with only a 15 percent 5-year survival rate for combined cancer stages. Challenges facing the current chemotherapy drugs include excessive toxicity to healthy tissues and limited ability to prevent metastases. A dual drug delivery system described herein selectively targets the lung to deliver anti-cancer drugs and inhibit the formation of metastases.

33 Claims, 13 Drawing Sheets
(6 of 13 Drawing Sheet(s) Filed in Color)

(56) References Cited

OTHER PUBLICATIONS

Chayen NE, Saridakis E. Protein crystallization: from purified protein to diffraction-quality crystal. Nature Methods. Feb. 2008;5(2):147-153.

Cheng Y, Prud'homme RK, Thomas JL. Diffusion of mesoscopic probes in aqueous polymer solutions measured by fluorescence recovery after photobleaching. Macromolecules. Oct. 8, 2002;35(21):8111-8121.

Chiu DT, Lorenz RM. Chemistry and Biology in Femtoliter and Picoliter Volume Droplets. Accounts of Chemical Research. 2009;42(5):649-658.

Chou T-C, Talalay P. Quantitative analysis of dose-effect relationships: the combined effects of multiple drugs or enzyme inhibitors. Advances in Enzyme Regulation. 1984;22:27-55.

Chou TC. Theoretical basis, experimental design, and computerized simulation of synergism and antagonism in drug combination studies. Pharmacological Reviews. Sep. 2006;58(3):621-681.

Chu LY, Utada AS, Shah RK, Kim JW, Weitz DA. Controllable monodisperse multiple emulsions. Angewandte Chemie—International Edition. 2007;46(47):8970-8974.

Committee NRN. A Unified Nomenclature System for the Nuclear Receptor Superfamily. Cell. 1999;97(2):161-163.

Davis MA, Taube RA. Pulmonary Perfusion Imaging: Acute Toxicity and Safety Factors as a Function of Particle Size. J Nucl Med. Nov. 1, 1978;19(11):1209-1213.

Deshmukh M, Chao P, Kutscher HL, Gao D, Sinko PJ. A Series of Œ±-Amino Acid Ester Prodrugs of Camptothecin: In Vitro Hydrolysis and A549 Human Lung Carcinoma Cell Cytotoxicity. Journal of Medicinal Chemistry. 2010;53(3):1038-1047.

Dharap SS, Qiu B, Williams GC, Sinko P, Stein S, Minko T. Molecular targeting of drug delivery systems to ovarian cancer by BH3 and LHRH peptides. Journal of Controlled Release. Aug. 2003;91(1-2):61-73.

Dharap SS, Wang Y, Chandna P, et al. Tumor-specific targeting of an anticancer drug delivery system by LHRH peptide. Proceedings of the National Academy of Sciences of the United States of America. Sep. 2005;102(36):12962-12967.

Doerschuk CM, Beyers N, Coxson HO, Wiggs B, Hogg JC. Comparison of neutrophil and capillary diameters and their relation to neutrophil sequestration in the lung. J Appl Physiol. Jun. 1993;74(6):3040-3045.

Downey GP, Doherty DE, Schwab B, 3rd, Elson EL, Henson PM, Worthen GS. Retention of leukocytes in capillaries: role of cell size and deformability. J Appl Physiol. Nov. 1990;69(5):1767-1778.

D'Souza AJM, Schowen RL, Topp EM. Polyvinylpyrrolidone-drug conjugate: Synthesis and release mechanism. Journal of Controlled Release. Jan. 2004;94(1):91-100.

D'Souza AJM, Topp EM. Release from polymeric prodrugs: Linkages and their degradation. Journal of Pharmaceutical Sciences. Aug. 2004;93(8):1962-1979.

Edd JF, Di Carlo D, Humphry KJ, et al. Controlled encapsulation of single-cells into monodisperse picolitre drops. Lab on a Chip. Aug. 2008;8(8):1262-1264.

Escriva H, Langlois M-C, Mendon<<A RL, Pierce R, Laudet V. Evolution and Diversification of the Nuclear Receptor Superfamily<sup>a</sup>. Annals of the New York Academy of Sciences. 1998;839(Trends in Comparative Endocrinology and Neurobiology: From Molecular to Integrative Biology):143-146.

Evans R. The steroid and thyroid hormone receptor superfamily. Science. May 13, 1988;240(4854):889-895.

Fakhrzadeh L, Laskin JD, Laskin DL. Regulation of caveolin-1 expression, nitric oxide production and tissue injury by tumor necrosis factor-alpha following ozone inhalation. Toxicology and Applied Pharmacology. Mar. 2008;227(3):380-389.

Fonovic M, Verhelst SHL, Sorum MT, Bogyo M. Proteomics evaluation of chemically cleavable activity-based probes. Molecular & Cellular Proteomics. 2007;6:1761-1770.

Fornal M, Lekka M, Pyka-Fosciak G, et al. Erythrocyte stiffness in diabetes mellitus studied with atomic force microscope. Clin Hemorheol Microcirc. 2006;35(1-2):273-276.

Gindy ME, Ji SX, Hoye TR, Panagiotopoulos AZ, Prud'homme RK. Preparation of Poly(ethylene glycol) Protected Nanoparticles with Variable Bioconjugate Ligand Density. Biomacromolecules. Oct. 2008;9(10):2705-2711.

Glass CK, Rosenfeld MG. The coregulator exchange in transcriptional functions of nuclear receptors. Genes & Development. 2000;14(2):121-141.

Goodrich, K., A. Yoshimura, et al. Measurement of the Modulus and Yield Strength of Soft Gels—Experiments and Numerical-Simulation (1989) Journal of Rheology 33(2): 317-327.

Greenwald RB, Choe YH, McGuire J, Conover CD. Effective drug delivery by PEGylated drug conjugates. Advanced Drug Delivery Reviews. 2003;55(2):217-250.

Greenwald RB, Pendri A, Choe YH, Inventors; Enzon, Inc., assignee. Polymeric prodrugs of amino- and hydroxyl-containing bioactive agents. U.S. Pat. No. 6,180,095.

Greenwald RB, Pendri A, Conover CD, et al. Drug delivery systems employing 1,4- or 1,6-elimination: Poly(ethylene glycol) prodrugs of amine-containing compounds. Journal of Medicinal Chemistry. 1999;42(18):3657-3667.

Gronemeyer H, Gustafsson J-A, Laudet V. Principles for modulation of the nuclear receptor superfamily. Nat Rev Drug Discov. 2004;3(11):950-964.

Gupta E, Vyas V, Ahmed F, Sinko P, Cook T, Rubin E. Pharmacokinetics of orally administered camptothecins. In: Liehr JG, Giovanella BC, Verschaegen CF, eds. Camptothecins: Unfolding Their Anticancer Potential. vol. 9222000:195-204.

Harris TD, Sworin M, Williams N, et al. Synthesis of Stable Hydrazones of a Hydrazinonicotinyl-Modified Peptide for the Preparation of 99mTc-Labeled Radiopharmaceuticals. Bioconjugate Chemistry. 1999;10(5):808-814.

Heinrich G, Straube E, Helmis G. Rubber Elasticity of Polymer Networks—Theories. Advances in Polymer Science. 1988;85:33-87.

Huang Y, Doerschuk CM, Kamm RD. Computational modeling of RBC and neutrophil transit through the pulmonary capillaries. J Appl Physiol. Feb. 2001;90(2):545-564.

Johnson BK, Prud'homme RK. Flash NanoPrecipitation of organic actives and block copolymers using a confined impinging jets mixer. Australian Journal of Chemistry. 2003;56(10):1021-1024.

Johnson BK, Prud'homme RK. Mechanism for rapid self-assembly of block copolymer nanoparticles. Physical Review Letters. Sep. 12, 2003;91(11).

Kang LF, Chung BG, Langer R, Khademhosseini A. Microfluidics for drug discovery and development: From target selection to product lifecycle management. Drug Discovery Today. Jan. 2008;13(1-2):1-13.

Kline TR, Runyon MK, Pothiawala M, Ismagilov RF. ABO, D blood typing and subtyping using plug-based microfluidics. Analytical Chemistry. Aug. 2008;80(16):6190-6197.

Klinge CM, Bodenner DL, Desai D, Niles RM, Traish AM. Binding of type II nuclear receptors and estrogen receptor to full and half-site estrogen response elements in vitro. Nucleic Acids Research. 1997;25(10):1903-1912.

Klinge CM. Estrogen receptor interaction with co-activators and co-repressors[small star, filled]. Steroids. 2000;65(5):227-251.

Kolhe P, Misra E, Kannan RM, Kannan S, Lieh-Lai M. Drug complexation, in vitro release and cellular entry of dendrimers and hyperbranched polymers. International Journal of Pharmaceutics. Jun. 2003;259(1-2):143-160.

Kumar R, Thompson EB. The structure of the nuclear hormone receptors. Steroids. 1999;64(5):310-319.

Kurtoglu YE, Navath RS, Wang B, Kannan S, Romero R, Kannan RM. Poly(amidoamine) dendrimer-drug conjugates with disulfide linkages for intracellular drug delivery. Biomaterials. Apr. 2009;30(11):2112-2121.

Lalloo A, Chao P, Hu P, Stein S, Sinko PJ. Pharmacokinetic and pharmacodynamic evaluation of a novel in situ forming poly(ethylene glycol)-based hydrogel for the controlled delivery of the camptothecins. Journal of Controlled Release. May 2006;112(3):333-342.

Lalloo AK, Luo FR, Guo A, et al. Membrane transport of camptothecin: Facilitation by human P-glycoprotein (ABCB1) and multidrug resistance protein 2 (ABCC2). BMC Medicine. 2004;2.

(56) References Cited

OTHER PUBLICATIONS

Laudet V. Evolution of the nuclear receptor superfamily: early diversification from an ancestral orphan receptor. J Mol Endocrinol. Dec. 1, 1997;19(3):207-226.
Lee ES, Na K, Bae YH. Polymeric micelle for tumor pH and folate-mediated targeting. J Control Release. Aug. 28, 2003;91(1-2):103-113.
Linja MJ, Porkka KP, Kang Z, et al. Expression of Androgen Receptor Coregulators in Prostate Cancer. Clinical Cancer Research. 2004;10(3):1032-1040.
Luo FR, Paranjpe PV, Guo A, Rubin E, Sinko P. Intestinal transport of irinotecan in Caco-2 cells and MDCK II cells overexpressing efflux transporters PGP, cMOAT, and MRP1. Drug Metabolism and Disposition. Jul. 2002;30(7):763-770.
Luo JK, Fu YQ, Li Y, et al. Moving-part-free microfluidic systems for lab-on-a-chip. Journal of Micromechanics and Microengineering. May 2009;19(5).
Mangelsdort DJ, Thummel C, Beato M, et al. The nuclear receptor superfamily: The second decade. Cell. 1995;83(6):835-839.
Mathieu A, Remmelink M, D'Haene N, et al. Development of a chemoresistant orthotopic human nonsmall cell lung carcinoma model in nude mice—Analyses of tumor heterogeneity in relation to the immunohistochemical levels of expression of cyclooxygenase-2, ornithine decarboxylase, lung-related resistance protein, prostaglandin E synthetase, and glutathione-S-transferase (GST)-alpha, GST-mu, and GST-pi. Cancer. Oct. 2004;101(8):1908-1918.
Mazzio EA, Soliman KF. Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-1184.
Minko T, Paranjpe PV, Qiu B, et al. Enhancing the anticancer efficacy of camptothecin using biotinylated poly(ethyleneglycol) conjugates in sensitive and multidrug-resistant human ovarian carcinoma cells. Cancer Chemotherapy and Pharmacology. Aug. 2002;50(2):143-150.
Modak N, Datta A, Ganguly R. Cell separation in a microfluidic channel using magnetic microspheres. Microfluidics and Nanofluidics. May 2009;6(5):647-660.
Mohan R, Heyman RA. Orphan Nuclear Receptor Modulators. Current Topics in Medicinal Chemistry. 2003;3(14):1637-1647.
Muller, I.A., Kratz, F., Jung, M., Warnecke, A. Schiff bases derived from p-aminobenzyl alcohol as trigger groups for pH-dependent prodrug activation. Tetrahedron Letters 51: 4371-4374.
Navath RS, Kurtoglu YE, Wang B, Kannan S, Romero R, Kannan RM. Dendrimer-Drug Conjugates for Tailored Intracellular Drug Release Based on Glutathione Levels. Bioconjugate Chemistry. Dec. 2008;19(12):2446-2455.
Nie ZH, Seo MS, Xu SQ, et al. Emulsification in a microfluidic flow-focusing device: effect of the viscosities of the liquids. Microfluidics and Nanofluidics. Nov. 2008;5(5):585-594.
Novac N, Heinzel T. Nuclear Receptors: Overview and Classification. Current Drug Targets—Inflammation & Allergy. 2004;3(4):335-346.
Olefsky JM. Nuclear Receptor Minireview Series. Journal of Biological Chemistry. 2001;276(40):36863-36864.
Onn A, Isobe T, Itasaka S, et al. Development of an orthotopic model to study the biology and therapy of primary human lung cancer in nude mice. Clinical Cancer Research. Nov. 2003;9(15):5532-5539.
Overington JP, Al-Lazikani B, Hopkins AL. How many drug targets are there? Nat Rev Drug Discov. 2006;5(12):993-996.
Panagiotou T, Mesite SV, Fisher RJ. Production of Norfloxacin Nanosuspensions Using Microfluidics Reaction Technology through Solvent/Antisolvent Crystallization. Industrial & Engineering Chemistry Research. Feb. 2009;48(4):1761-1771.
Paranjpe PV, Chen Y, Kholodovych V, Welsh W, Stein S, Sinka PJ. Tumor-targeted bioconjugate based delivery of camptothecin: design, synthesis and in vitro evaluation. Journal of Controlled Release. Nov. 2004;100(2):275-292.

Pascual G, Glass CK. Nuclear receptors versus inflammation: mechanisms of transrepression. Trends in Endocrinology & Metabolism. 2006;17(8):321-327.
Rajendra R, Gounder MK, Saleem A, et al. Differential effects of the breast cancer resistance protein on the cellular accumulation and cytotoxicity of 9-aminocamptothecin and 9-nitrocamptothecin. Cancer Research. Jun. 2003;63(12):3228-3233.
Sauter C, Dhouib K, Lorber B. From macrofluidics to microfluidics for the crystallization of biological macromolecules. Crystal Growth & Design. Nov. 2007;7(11):2247-2250.
Selimovic S, Jia YW, Fraden S. Measuring the Nucleation Rate of Lysozyme using Microfluidics. Crystal Growth & Design. Apr. 2009;9(4):1806-1810. Senter PD, Pearce WE, Greenfield RS. Development of a Drug-Release Strategy Based on the Reductive Fragmentation of Benzyl Carbamate Disulfides. Journal of Organic Chemistry. 1990;55(9):2975-2978.
Shiau AK, Barstad D, Loria PM, et al. The Structural Basis of Estrogen Receptor/Coactivator Recognition and the Antagonism of This Interaction by Tamoxifen. Cell. 1998;95(7):927-937.
Sluder AE, Maina CV. Nuclear receptors in nematodes: themes and variations. Trends in Genetics. 2001;17(4):206-213.
Smith CL, O'Malley BW. Coregulator Function: A Key to Understanding Tissue Specificity of Selective Receptor Modulators. Endocr Rev. Feb. 1, 2004;25(1):45-71.
Srisa-Art M, Dyson EC, Demello AJ, Edel JB. Monitoring of real-time streptavidin-biotin binding kinetics using droplet microfluidics. Analytical Chemistry. Sep. 2008;80(18):7063-7067.
Stone HA, Kim S. Microfluidics: Basic issues, applications, and challenges. Aiche Journal. Jun. 2001;47(6)1250-1254.
Stone HA, Stroock AD, Ajdari A. Engineering flows in small devices: Microfluidics toward a lab-on-a-chip. Annual Review of Fluid Mechanics. 2004;36:381-411.
Su YM, Zhang XP, Sinko PJ. Exploitation of drug-induced Bcl-2 overexpression for restoring normal apoptosis function: A promising new approach to the treatment of multidrug resistant cancer. Cancer Letters. Aug. 2007;253(1):115-123.
Sunil VR, Laumbach RJ, Patel KJ, et al. Pulmonary effects of inhaled limonene ozone reaction products in elderly rats. Toxicology and Applied Pharmacology. Jul. 2007;222(2):211-220.
Sunil VR, Patel KJ, Mainelis G, et al. Pulmonary effects of inhaled diesel exhaust in aged mice. Toxicology and Applied Pharmacology. Dec. 2009;241(3):283-293.
Tata JR. One hundred years of hormones. EMBO reports. 2005;6(6):490-496.
Teh SY, Lin R, Hung LH, Lee AP. Droplet microfluidics. Lab on a Chip. 2008;8(2):198-220.
Umbanhowar PB, Prasad V, Weitz DA. Monodisperse emulsion generation via drop break off in a coflowing stream. Langmuir. Jan. 2000;16(2):347-351.
Ungun B, Prud'homme RK, Budijono SJ, et al. Nanofabricated upconversion nanoparticles for photodynamic therapy. Optics Express. Jan. 2009;17(1):80-86.
Vladisavljevic GT, Kobayashi I, Nakajima M, Williams RA, Shimizu M, Nakashima T. Shirasu Porous Glass membrane emulsification: Characterisation of membrane structure by high-resolution X-ray microtomography and microscopic observation of droplet formation in real time. Journal of Membrane Science. Sep. 2007;302(1-2):243-253.
Vladisavljevic GT, Tesch S, Schubert H. Preparation of water-in-oil emulsions using microporous polypropylene hollow fibers: influence of some operating parameters on droplet size distribution. Chemical Engineering and Processing. 2002;41(3):231-238.
Vortherms AR, Doyle RP, Gao D, Debrah O, Sinko PJ. Synthesis, characterization, and in vitro assay of folic acid conjugates of 3'-azido-3'-deoxythymidine (AZT): Toward targeted AZT based anti-cancer therapeutics. Nucleosides Nucleotides & Nucleic Acids. 2008;27(2):173-185.
Wan L, Zhang X, Gunaseelan S, et al. Novel multi-component nanopharmaceuticals derived from poly(ethylene) glycol, retro-inverso-Tat nonapeptide and saquinavir demonstrate combined anti-HIV effects. AIDS Research and Therapy. 2006;3(1).

(56) References Cited

OTHER PUBLICATIONS

Warnmark A, Treuter E, Wright APH, Gustafsson J-A. Activation Functions 1 and 2 of Nuclear Receptors: Molecular Strategies for Transcriptional Activation. Mol Endocrinol. Oct. 1, 2003;17(10):1901-1909.

Welch CF, Rose GD, Malotky D, Eckersley ST. Rheology of high internal phase emulsions. Langmuir. Feb. 2006;22(4):1544-1550.

Wiggs BR, English D, Quinlan WM, Doyle NA, Hogg JC, Doerschuk CM. Contributions of capillary pathway size and neutrophil deformability to neutrophil transit through rabbit lungs. J Appl Physiol. Jul. 1994;77(1):463-470.

Wortham M, Czerwinski M, He L, Parkinson A, Wan Y-JY. Expression of Constitutive Androstane Receptor, Hepatic Nuclear Factor 4Œ±, and P450 Oxidoreductase Genes Determines Interindividual Variability in Basal Expression and Activity of a Broad Scope of Xenobiotic Metabolism Genes in the Human Liver. Drug Metabolism and Disposition. 2007;35(9):1700-1710.

Wu W, Niles E, Hirai H, LoVerde P. Evolution of a novel subfamily of nuclear receptors with members that each contain two DNA binding domains. BMC Evolutionary Biology. 2007;7(1):27.

Wu W, Niles EG, El-Sayed N, Berriman M, LoVerde PT. Schistosoma mansoni (Platyhelminthes, Trematoda) nuclear receptors: Sixteen new members and a novel subfamily. Gene. 2006;366(2):303-315.

Yin YL, Prudhomme RK, Stanley F. Relationship between Poly(Acrylic Acid) Gel Structure and Synthesis. Acs Symposium Series. 1992;480:91-113.

Zhang Z, Burch PE, Cooney AJ, et al. Genomic Analysis of the Nuclear Receptor Family: New Insights Into Structure, Regulation, and Evolution From the Rat Genome. Genome Research. 2004;14(4):580-590.

Zivadinovic D, Gametchu B, Watson C. Membrane estrogen receptor-alpha levels in MCF-7 breast cancer cells predict cAMP and proliferation responses. Breast Cancer Res. 2005;7(1):R101-R112.

Chao PY, Deshmukh M, Kutscher HL, et al. Pulmonary targeting microparticulate camptothecin delivery system: anticancer evaluation in a rat orthotopic lung cancer model. Anti-Cancer Drugs. Jan. 2010;21(1):65-76.

Choe YH, Greenwald RB, Conover CD, et al. PEG prodrugs of 6-mercaptopurine for parenteral administration using benzyl elimination of thiols. Oncology Research. 2004;14(9):455-468.

Chou T-C. Preclinical versus clinical drug combination studies. Leukemia & Lymphoma. 2008;49(11):2059-2080.

Haggerty L, Sugarman JH, Prudhomme RK. Diffusion of Polymers through Polyacrylamide Gels. Polymer. Jun. 1988;29(6):1058-1063.

Paranjpe PV, Stein S, Sinko PJ. Tumor-targeted and activated bioconjugates for improved camptothecin delivery. Anti-Cancer Drugs. 2005;16(7):763-775.

Schanker LS, Less MJ. Lung pH and pulmonary absorption of nonvolatile drugs in the rat. Drug Metab Dispos. Mar.-Apr. 1977;5(2):174-178.

Schroeder HG, Bivins BA, Sherman GP, DeLuca PP. Physiological effects of subvisible microspheres administered intravenously to beagle dogs. J Pharm Sci. Apr. 1978;67(4):508-513.

Ye L, Jing XZ, Yang H, Su JT, Yun LH. Complex and in vitro release of methotrexate-PAMAM dendrimer. Chemical Journal of Chinese Universities—Chinese. Feb. 2005;26(2):353-355.

Gupta E, Luo F, Lallo A, et al. The intestinal absorption of camptothecin, a highly lipophilic drug, across Caco-2 cells is mediated by active transporter(s). Anticancer Research. Mar.-Apr. 2000;20(2A):1013-1016. Abstract Only.

Gupta E, Cook TJ, Rubin EH, Sinko PJ. Characterization and in vitro in vivo correlation of the intestinal permeability of 20(S) camptothecin (CPT). Faseb Journal. Feb. 1997;11(3):1737-1737. (Unavailable).

Wolfson T. Composite nanoparticles for MRI imaging. Senior Thesis Princeton University. 2008. (Unavailable).

\* cited by examiner

FIG. 7A, B, C, AND D

CAMPTOTHECIN
PACLITAXEL

LUNG TARGETING DUAL DRUG DELIVERY SYSTEM

CROSS REFERENCE TO RELATED APPLICATIONS

This application claims the benefit of U.S. provisional application No. 61/320,941 filed Apr. 5, 2010, which is incorporated herein by reference as if fully set forth.

This invention was made with government support under Grant CTS-0506966 awarded by the National Science Foundation and Grant AI051214 awarded by the National Institutes of Health. The government has certain rights in this invention.

FIELD OF INVENTION

The disclosure herein relates to a drug delivery system.

BACKGROUND

Previously, the American Cancer Society estimated that 1,479,350 new cancer cases would be diagnosed in the United States during 2009 of which 219,440 would be lung and bronchus related. Although only the second most prevalent type of cancer, behind prostate and breast cancer for men and women respectively, lung cancer is the most lethal accounting for a projected 159,390 deaths in the United States. Non-small cell lung cancer (NSCLC), a subset of lung cancer, encompasses a set of diseases with similar prognosis and treatments. The standard treatments for NSCLC include surgery, chemotherapy, radiation, laser and photodynamic therapy, all with various success rates depending on the stage of the cancer. Many current chemotherapy drugs also have excessive toxicity to healthy tissues and a limited ability to prevent metastases.

Despite recent advances in molecular characterization and targeted and adjuvant therapies, surgical resection remains the mainstay of curative treatment for NSCLC. Unfortunately, less than one third of NSCLC patients present with resectable disease. Neoadjuvant chemotherapy alone or with concurrent radiation is often used for stage IIIA NSCLC but is often tried in patients with stage IIIB and at times in patients with stage I or II disease.

After the initial diagnosis, more than half of the patients with localized lung cancer survive at least 5 years. But the general prognosis of NSCLC patients remains poor and unpredictable due to the high invasiveness potential of the disease. The National Cancer Institute assesses that results of standard treatment are generally poor with only a 15 percent 5-year survival rate for combined cancer stages.

SUMMARY

In an aspect, the invention relates to a delivery system comprising a gel microparticle, a plurality of nanoparticles associated with the gel microparticle, and one or more drugs associated with at least one of the nanoparticles.

In an aspect, the invention relates to a method of treating a condition comprising administering a delivery system to a patient in need thereof. The delivery system includes a gel microparticle, a plurality of nanoparticles associated with the gel microparticle, and one or more drugs associated with at least one of the nanoparticles.

In an aspect, the invention relates to a method of making the delivery system. The delivery system includes a gel microparticle, a plurality of nanoparticles associated with the gel microparticle, and one or more drugs associated with the nanoparticles. The method includes synthesizing the nanoparticles to be loaded with the one or more drugs; and associating the nanoparticles with the gel microparticles.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of the preferred embodiment of the present invention will be better understood when read in conjunction with the appended drawings. For the purpose of illustrating the invention, there are shown in the drawings embodiments, which are presently preferred. It is understood, however, that the invention is not limited to the precise arrangements and instrumentalities shown. In the drawings.

DETAILED DESCRIPTION OF THE PREFERRED EMBODIMENTS

Figure 1:
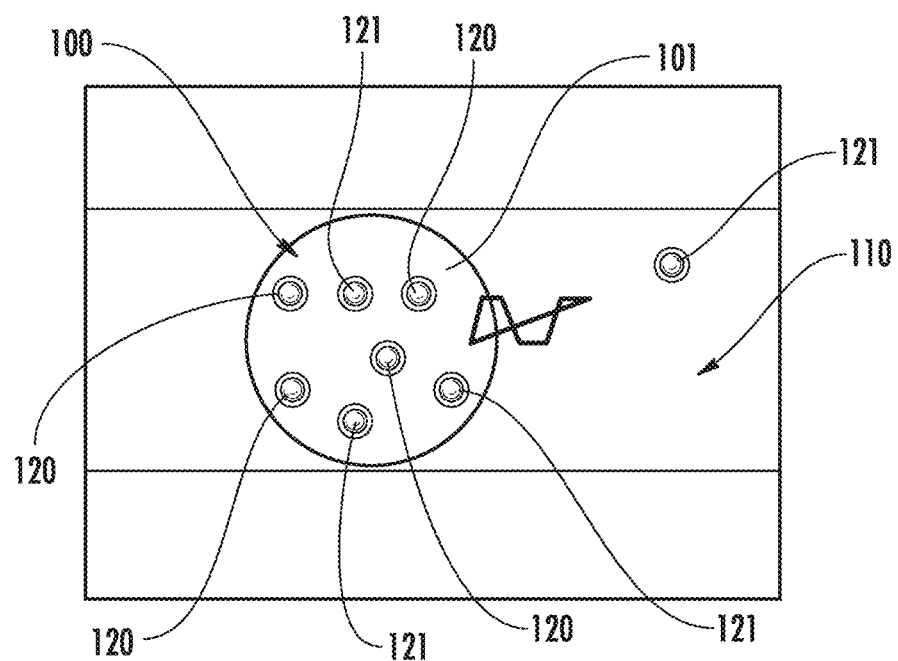
FIG. 1 illustrates a gel microparticle trapped in a lung capillary with drug loaded nanoparticles embedded in the gel microparticle. The nanoparticles may be released overtime in the lung to kill cancer cells, TB mycobacteria or to treat asthma.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. The phrase "at least one" followed by a list of two or more items, such as "A, B, or C," means any individual one of A, B or C as well as any combination thereof.

The design of the human lung affords unique targeting options. An embodiment includes passive targeting of the lung via the venous blood stream. The lung receives the entire venous blood supply from the heart and passes it through the intricate capillary beds on the alveoli. Large particles in the venous blood are thus trapped in these capillary beds. This filtering phenomenon can be used to selectively deliver particles to the lung. The use of this novel delivery route for chemotherapeutic drugs has not been appreciated or utilized by the drug delivery community. Nor has this delivery route been used for the delivery of TB, asthma, or chronic obstructive pulmonary disease (COPD) therapeutic drugs. An embodiment includes targeting agents to the liver with a delivery system herein. An embodiment includes targeting agents to the spleen with a delivery system herein. An embodiment includes targeting agents to the kidney with a delivery system herein. An embodiment includes targeting agents to tumors with a delivery system herein. An embodiment includes targeting agents to lymph nodes with a delivery system herein. Microparticles can be targeted to the lung, liver, and spleen via intravenous injection based on size (the lung is the filter with the largest pores, the liver is the next smallest filter and the spleen is the smallest of the three). Arterial injections favor the liver. Microparticles can also be filtered out by tumors and the lymph nodes.

Referring to FIG. 1, a delivery system 100 is illustrated having a gel microparticle 101 and nanoparticles 120, 121. The delivery system 100 is shown within a capillary 110. A delivery system may include one or more kind of nanoparticles. In the embodiment illustrated, two kinds of nanoparticles are illustrated as nanoparticles 120 and nanoparticles 121. The different kinds of nanoparticles may vary based on at least one of physical or chemical characteristics of the different nanoparticles themselves. The different kinds of nanoparticles may vary based on at least one of the presence or absence of drug(s) loaded on or in the different nanoparticles, the presence or absence of targeting moieties on or in the different nanoparticles or the presence or absence of chemopotentiators loaded on or in the nanoparticles. These variations are non-limiting examples of ways different nanoparticle populations in a gel microparticle may vary.

An embodiment includes a delivery system comprising a gel microparticle, a plurality of nanoparticles associated with the gel microparticle, and one or more drugs associated with the nanoparticles. The plurality of nanoparticles may be associated with the gel microparticle by being at least one of on or in the gel microparticle. A delivery system may also include at least one of one or more targeting agent or one or more chemopotentiator.

An embodiment includes nanoparticles as drug "sources" and uses thereof. In the presence of a lypophylic sink, the drug molecules, encapsulated in the nanoparticle, may partition into the matrix of the gel microparticle and diffuse to the sink.

The gel microparticle may include degradable linkages between individual polymers of a co-polymer. The degradable linkages between polymers in a gel microparticle can be but are not limited to ester degradable linkages, ketal degradable linkages, acetal degradable linkages, enzymatically degradable linkages, linkages degraded by reducing or oxidizing reactions and degradable orthoester linkages. The degradable linkages in a gel microparticle can be all of one kind or more than one kind. The more than one kind can be selected from the preceding degradable linkages. A gel microparticle may have any suitable size to be retained in a target capillary. Gel microparticles may have a size of 1 μm to 60 μm. The shear modulus of a microparticle may be any value, but could be selected in combination with the particle size to optimize retention in the desired site of therapeutic action. The shear modulus of a gel microparticle may be between 4 Pa and 200,000 Pa. The shear modulus of a gel microparticle may have any integer value from 4 Pa to 200,000 Pa. The shear modulus of a gel microparticle may be in a range between and including any two integer values from 4 Pa to 200,000 Pa, or may have any value in a range between and including any two integer values from 4 Pa to 200,000 Pa. The shear modulus of the microparticle may be determined by forming a gel using the same chemical formulation as in the dispersed phase of the emulsion, polymerizing said gel phase, and measuring the shear modulus or storage modulus of the gel using rheological instrumentation such as are standard in the materials characterization field. Measurement of this type are described in Goodrich, K., A. Yoshimura, et al. Measurement of the Modulus and Yield Strength of Soft Gels—Experiments and Numerical-Simulation (1989) Journal of Rheology 33(2): 317-327, which is incorporated herein by reference as if fully set forth. The gel microparticles may include biocompatible, aqueous-soluble polymers. The gel microparticles may include functionalized, crosslinkable, biocompatible polymers. The gel microparticles may include polymers formed from functionalized poly(2-hydroxyethyl methacrylate) polymers. The gel microparticles may include polymers formed from functionalized polyphosphate polymers. The gel microparticles may include polymers formed from functionalized PEG polymers or copolymers. The gel microparticles may include polymers formed from functionalized dextran polymers. The gel microparticles may include polymers formed from functionalized polyvinyl pyrrolidone polymers or co-polymers. The gel microparticles may include polymers formed from functionalized polyacrylic acid polymers or copolymers. The gel microparticles may include polymers formed from functionalized poly(amine) or poly (amide) polymers or copolymers. Examples of these include but are not limited to DMAEMA and NIPAam. NIPAam may be utilized to provide temperature sensitive moieties.

The gel microparticle polymers may be formed into gels by a free radical polymerization process. The gel microparticle polymers may be formed into gels by a mannich linking reaction. The gel microparticle polymers may be formed into gels by a process of hydrophobic association. The gel microparticle polymers may be formed into gels by a cation mediated complex formation process. The gel microparticle polymers may be formed into gels by an ester, amide, or disulfide crosslink between at least a portion of the polymers. The gel microparticle polymers may be formed into gels by crosslink cinnamoyl groups.

The gel microparticle polymers may include functionalized PEG polymers having a molecular weight from 200 to 200,000 g/mole. The gel microparticle polymers may include functionalized PEG polymers with a molecular weight having any specific integer value in the range from 200 to 200,000 g/mole. The gel microparticle polymers may include functionalized PEG polymers having a molecular weight in a range between and including any two specific integer values in the range from 200 to 200,000 g/mole. The gel microparticle polymers may include functionalized PEG polymer having a molecular weight of any value in a range between and including any two integer values from 200 to 200,000 g/mole. The gel microparticle polymers may include functionalized dextran polymers having a molecular weight from 200 to 100,000 g/mole. The gel microparticle polymers may include functionalized dextran polymers with a molecular weight having any specific integer value in the range from 200 to 100,000 g/mole. The gel microparticle polymers may include functionalized dextran polymers with a molecular weight in a range between and including any two specific integer values in the range from 200 to 100,000 g/mole. The gel microparticle polymers may include functionalized dextran polymers having a molecular weight of any value in a range between and including any two integer values from 200 to 200,000 g/mole. The gel microparticle polymers may include functionalized polyvinyl pyrrolidone polymers or copolymers having a molecular weight from 200 to 100,000 g/mole. The gel microparticle polymers may include functionalized polyvinyl pyrrolidone polymers or copolymers with a molecular weight having any specific integer value in the range from 200 to 100,000 g/mole. The gel microparticle polymers may include functionalized polyvinyl pyrrolidone polymers or copolymers with a molecular weight in a range between and including any two specific integer values in the range from 200 to 100,000 g/mole. The gel microparticle polymers may include functionalized polyvinyl pyrrolidone polymers having a molecular weight of any value in a range between and including any two integer values from 200 to 200,000 g/mole. The gel microparticle polymers may include polymers formed from PLA-PEG-PLA macromers.

The nanoparticles may include PEG protective coatings. The plurality of nanoparticles may be associated with the gel microparticle by any physical combination. The plurality of nanoparticles may be associated with the gel microparticle by being mixed with the material of the gel microparticle. The plurality of nanoparticles may be associated with the gel microparticle by being imbedded in the microparticle. The plurality of nanoparticles may be associated with the gel microparticle on the surface of the microparticle. The plurality of nanoparticles may be associated with the gel microparticle by being chemically linked to the gel microparticle. The chemical linkage may be covalent. The chemical linkage may be degradable. The degradable linkages between a nanoparticle and material of a gel microparticle can be but are not limited to ester degradable linkages, ketal degradable linkages, acetal degradable linkages, enzymatically degradable linkages, linkages degraded by reducing or oxidizing reactions and degradable orthoester linkages. The degradable linkages between a nanoparticles and gel microparticle can be all of one kind or more than one kind. The more than one kind can be selected from the preceding list of degradable linkages.

The one or more drugs in a delivery system may be active to combat any target disease. The list of drugs that could be included in a delivery system includes any therapeutic agent that is selected for targeting through passive targeting with a gel microparticle.

The one or more drugs may include a cancer therapeutic agent. The one or more drugs may include a non-small cell lung cancer (NSCLC) therapeutic agent. The one or more drugs may include at least one of signal transduction inhibitors, cytotoxic agents, cell cycle inhibitors, cell cycle control inhibitors, checkpoint inhibitors that interfere with the normal function of cell cycle checkpoints, checkpoint inhibitors that interfere with the normal function of cell cycle S/G2 checkpoint, checkpoint inhibitors that interfere with the normal function of cell cycle G2/M checkpoint, checkpoint inhibitors that interfere with the normal function of cell cycle G1/S checkpoint, topoisomerase inhibitors, camptothecins, enzymes necessary for DNA replication, enzymes necessary for DNA transcription, receptor tyrosine kinase inhibitors, apoptosis inducing agents, antimetabolites, gemcitabine, hydroxyurea, telomerase inhibitors, cyclin-dependent kinase inhibitors, cytoskeletal proteins, transcription factors, tumor suppresser genes, DNA damaging agents, DNA repair inhibitors, anti-angiogenic agents or mitochondrial poisons. The one or more drugs may include at least one of DNA damaging agents, carboplatin, cisplatin, cyclophosphamide, doxorubicin, daunorubicin, epirubicin, mitomycin C, mitoxantrone, DNA repair inhibitors, 5-fluorouracil (5-FU), FUDR, gemcitabine, methotrexate, topoisomerase I inhibitors, camptothecin, irinotecan, topotecan, S/G2 checkpoint inhibitors, G2/M checkpoint inhibitors, bleomycin, docetaxel, doxorubicin, etoposide, paclitaxel, vinblastine, vincristine, vindesine, vinorelbine, G1/early-S checkpoint inhibitors, receptor tyrosine kinase inhibitors, genistein, trastuzumab, ZD1839, cytotoxic agents, apoptosis-inducing agents or cell cycle control inhibitors. One or more drugs above could be employed in as anti-cancer therapeutic agents in a delivery system or method herein. One or more drugs above could be employed in NSCLC therapeutic agents in a delivery system or method herein.

The one or more drugs may include a tuberculosis (TB) therapeutic agent. The one or more drug may include at least one of ethambutol (EMB or E), isoniazid, pyrazinamide, rifampicin, streptomycin, aminoglycosides, amikacin (AMK), kanamycin (KM), polypeptides, capreomycin, viomycin, enviomycin, fluoroquinolones, ciprofloxacin (CIP), levofloxacin, moxifloxacin (MXF), thioamides, ethionamide, prothionamide, cycloserine, p-aminosalicylic acid (PAS or P), rifabutin, macrolides, clarithromycin (CLR), linezolid (LZD), thioacetazone (T), thioridazine, arginine, vitamin D, R207910 or SQ641. One or more drugs above could be employed in as tuberculosis therapeutic agents in a delivery system or method herein.

The one or more drugs may include an asthma or chronic obstructive pulmonary disease (COPD) therapeutic agent. The one or more drug may include at least one of short-acting, selective $beta_2$-adrenoceptor agonists; adrenergic agonists; anticholinergic medications and long-acting $\beta_2$-agonists. One or more drugs above could be employed in as asthma or COPD therapeutic agents in a delivery system or method herein.

The one or more drugs may be loaded into a nanoparticle by flash nanoprecipitation. A targeting agent could also be loaded into a nanoparticle by flash nanoprecipitation.

A targeting agent could be associated with a nanoparticle by any physical or chemical association. A targeting agent could be associated with a nanoparticle through degradable linkages between the targeting agent and the nanoparticle. The degradable linkages between a targeting agent and a nanoparticle can be but are not limited to ester degradable linkages, ketal degradable linkages, acetal degradable linkages, enzymatically degradable linkages, linkages degraded by reducing or oxidizing reactions and degradable orthoester linkages. The degradable linkages in a between a targeting agent and a nanoparticle can be all of one kind or more than one kind. The more than one kind can be selected from at least one of the preceding list of degradable linkages.

As set forth above, individual polymers of a co-polymer in a microparticle, connections between nanoparticles and microparticles and connections between targeting agents and nanoparticles may be through degradable linkages. Any one component of the delivery system herein may also be associated another component through a degradable linkage. Examples of degradable linkages have been described in following references, which are incorporated herein by reference as if fully set forth and intended as representative and not exhaustive or limiting:

Harris T D, Sworin M, Williams N, et al. Synthesis of Stable Hydrazones of a Hydrazinonicotinyl-Modified Peptide for the Preparation of 99 mTc-Labeled Radiopharmaceuticals. Bioconjugate Chemistry. 1999; 10(5):808-814.

Choe Y H, Greenwald R B, Conover C D, et al. PEG prodrugs of 6-mercaptopurine for parenteral administration using benzyl elimination of thiols. Oncology Research. 2004; 14(9):455-468.

Fonovic M, Verhelst S H L, Sorum M T, Bogyo M. Proteomics evaluation of chemically cleavable activity-based probes. Molecular & Cellular Proteomics. 2007; 6:1761-1770.

Greenwald R B, Choe Y H, McGuire J, Conover C D. Effective drug delivery by PEGylated drug conjugates. Advanced Drug Delivery Reviews. 2003; 55(2):217-250.

Greenwald R B, Pendri A, Choe Y H, Inventors; Enzon, Inc., assignee. Polymeric prodrugs of amino- and hydroxyl-containing bioactive agents. U.S. Pat. No. 6,180,095.

Greenwald R B, Pendri A, Conover C D, et al. Drug delivery systems employing 1,4- or 1,6-elimination: Poly(ethylene glycol) prodrugs of amine-containing compounds. Journal of Medicinal Chemistry. 1999; 42(18):3657-3667.

Muller, I. A., Kratz, F., Jung, M., Warnecke, A. Schiff bases derived from p-aminobenzyl alcohol as trigger groups for pH-dependent prodrug activation. Tetrahedron Letters 51: 4371-4374.

Senter P D, Pearce W E, Greenfield R S. DEVELOPMENT OF A DRUG-RELEASE STRATEGY BASED ON THE REDUCTIVE FRAGMENTATION OF BENZYL CARBAMATE DISULFIDES. Journal of Organic Chemistry. 1990; 55(9):2975-2978.

D'Souza A J M, Schowen R L, Topp E M. Polyvinylpyrrolidone-drug conjugate: Synthesis and release mechanism. Journal of Controlled Release. January 2004; 94(1):91-100.

D'Souza A J M, Topp E M. Release from polymeric prodrugs: Linkages and their degradation. Journal of Pharmaceutical Sciences. August 2004; 93(8):1962-1979.

Kolhe P, Misra E, Kannan R M, Kannan S, Lieh-Lai M. Drug complexation, in vitro release and cellular entry of dendrimers and hyperbranched polymers. International Journal of Pharmaceutics. June 2003; 259(1-2):143-160.

Kurtoglu Y E, Navath R S, Wang B, Kannan S, Romero R, Kannan R M. Poly(amidoamine) dendrimer-drug conjugates with disulfide linkages for intracellular drug delivery. Biomaterials. April 2009; 30(11):2112-2121.

Navath R S, Kurtoglu Y E, Wang B, Kannan S, Romero R, Kannan R M. Dendrimer-Drug Conjugates for Tailored Intracellular Drug Release Based on Glutathione Levels. Bioconjugate Chemistry. December 2008; 19(12):2446-2455.

Ye L, Jing X Z, Yang H, Su J T, Yun L H. Complex and in vitro release of methotrexate-PAMAM dendrimer. Chemical Journal of Chinese Universities-Chinese. February 2005; 26(2):353-355.

A drug may be included in the gel microparticle. The association between a drug and a gel microparticle may be similar to an association described with respect to a drug and a nanoparticle. A targeting agent may be included in a gel microparticle. The association between a targeting agent and a gel microparticle may be similar to an association described with respect to a targeting agent and a nanoparticle. A chemopotentiator may be associated with at least one of a nanoparticle or a gel microparticle. The association between a chemopotentiator and a gel microparticle or nanoparticle may be similar to an association described with respect to a drug and a nanoparticle.

An embodiment includes a method of treating a condition comprising administering any one or more delivery system herein to a patient in need thereof. The step of administering may include intravenous injection. The step of administering may include intra-arterial injection.

An embodiment includes a method of making a delivery system herein having steps of: synthesizing the nanoparticles to be loaded with the one or more drugs; and forming micron sized aqueous particles by mixing functionalized polymers, the nanoparticles, crosslinking initiator and solvent in a hydrophobic fluid. The method may include loading the nanoparticles with at least one of one or more drug, one or more targeting agent or one or more chemopotentiator. An embodiment includes a method of making a delivery system herein having steps of: synthesizing nanoparticles and loading nanoparticles with the one or more drugs, and optionally one at least one of one or more targeting agent and one or more chemopotentiator; mixing functionalized polymers, the nanoparticles, crosslinking initiator and solvent to form the discontinuous phase; providing a hydrophobic fluid as the continuous phase; making small droplets using emulsification techniques, wherein the small droplets contain functionalized macromers, the nanoparticles, crosslinking initiator and solvent; and crosslinking the droplets. Droplets may be made in the size range 1-100 microns (endpoints included). Droplets may be made in the size range 5-40 microns in size (endpoints included). Droplets may be made in a range of any size between and including any integer value from 1 micron to 100 microns. A droplet may be made in any size in a range between and including any two integer values from 1 micron to 100 microns. An embodiment includes a method of making a delivery system herein having steps of: synthesizing the nanoparticles and loading the nanoparticles with the one or more drugs, and optionally at least one of one or more targeting agents or one or more chemopotentiator; mixing functionalized polymers, the nanoparticles, crosslinking initiator and solvent to form an inner liquid filament; providing a hydrophobic fluid with crosslinking initiator as a sheath fluid; flowing the sheath fluid past the inner liquid filament, and crosslinking droplets. An embodiment includes a method of making a delivery system herein having steps of synthesizing the nanoparticles and loading the nanoparticles with the one or more drugs, and optionally at least one of one or more targeting agents or one or more chemopotentiator; mixing functionalized polymers, the nanoparticles, crosslinking initiator and solvent to form the discontinuous phase; providing a hydrophobic fluid with crosslinking initiator as the continuous phase; using emulsification techniques to make small droplets containing functionalized macromers, the nanoparticles, crosslinking initiator and solvent; and crosslinking the droplets. In an embodiment surfactants are provided as a droplet stabilizing agent.

Methods of making a delivery system herein may provide one or more hydrophobic drug where the step of synthesizing the nanoparticles and loading with the one or more drugs may includes mixing the at least one of the one or more drugs with amphiphillic block copolymers in a water-miscible organic solvent. The methods then may include micromixing at least a portion of the mixture formed when synthesizing nanoparticles against water to produce supersaturations that drive rapid precipitation of the at least one of the one or more hydrophobic drugs and hydrophobic portions of the amphiphillic block copolymers.

Methods of making a delivery system herein may provide one or more targeting agents. The targeting agents may be included in the delivery system by mixing the at least one of the one or more targeting agents with amphiphillic block copolymers in a water-miscible organic solvent. The methods may then include micromixing at least a portion of the mixture formed when synthesizing nanoparticles against water to produce supersaturations that drive rapid precipitation of the at least one of the one or more targeting agents and hydrophobic portions of the amphiphillic block copolymers.

Methods of making a delivery system herein may provide one or more chemopotentiators. The chemopotentiators may be included in the delivery system by mixing the at least one of the one or more chemopotentiators with amphiphillic block copolymers in a water-miscible organic solvent. The methods may then include micromixing at least a portion of the mixture formed when synthesizing nanoparticles against water to produce supersaturations that drive rapid precipitation of the at least one of the one or more chemopotentiators and hydrophobic portions of the amphiphillic block copolymers.

Methods of making a delivery system herein may include forming the nanoparticles with functionalized groups and attaching at least one of the one or more drugs, the one or more targeting agents or the one or more chemopotentiators to the functionalized groups.

An embodiment includes a delivery system that employs both passive and active targeting to intravenously deliver drugs. A first layer of the delivery system is a gel microparticle (GMP or MP) designed to take advantage of the venous lung filtration pathway or liver filtration pathway and passively accumulates gel particles in the lungs or liver after injection into the body. Intravenous injection may be utilized to deliver particles to the lung, liver or spleen. Intra-arterial injection may be used to deliver particles to the liver, spleen or kidney. Any route of administration is contemplated. A second layer of the delivery system consists of nanoparticles (NP) embedded in the GMP. As set forth above, the delivery system may include drugs.

NP surfaces can be decorated with ligands to actively target cancer cells. An NP can be loaded with drugs for treatment of any ailment. As set forth above, an NP can be loaded with an anti-cancer drug(s), asthma or COPD drugs, or with anti-TB drug(s). A plurality of different drugs may be provided on the same or different nanoparticles included in one gel microparticle. A mix of different kinds of gel microparticles may be provided where each kind of gel microparticle has a different type of nanoparticle. A plurality different targeting agents may be provided on the same or different nanoparticles. If desired, the release rate of the NPs from the GMPs into a site; e.g., a tumor, and the release rate of a drug; e.g., an anti-cancer drug, from the NPs can be tuned to achieve the maximum desired effect. The dual-delivery system may provide the ability to sustain a high concentration of drugs in a site; e.g., the lungs or liver, while minimizing the systemic exposure and accordingly reducing the side effects.

The delivery systems herein are versatile. A combination of gel microparticle and nanoparticles(s) can be adapted to incorporate known anti-cancer drugs, known anti-TB drugs, known targeting agents, novel anti-cancer drugs as they are developed, or novel targeting agents as they are developed. NPs loaded with a newly developed or novel drug or a newly developed or novel targeting agent may be used for a delivery system or method herein.

An embodiment provides a delivery system and methods for the treatment of non-small cell lung cancer (NSCLC). The drug-delivery system and methods may deliver anti-cancer drugs by using both passive and active targeting. A method for treating NSCLC includes administering a delivery system including a nanoparticle with one or more drug that is an NSCLC therapeutic agent to a patient. The delivery system employed in the methods of treating NSCLC may include at least one of one or more targeting agent specific for NSCLC treatment or one or more chemopotentiator on a nanoparticle including the one or more drug that is an NSCLC therapeutic agent.

An embodiment provides a delivery system and methods for the treatment of TB. The drug-delivery system and methods may deliver TB drugs by using both passive and active targeting. A method for treating TB includes administering a delivery system including a nanoparticle with one or more drug that is a TB therapeutic agent to a patient. The delivery system employed in the methods of treating TB may include one or more targeting agent specific for TB treatment on a nanoparticle including the one or more drug that is a TB therapeutic agent.

An embodiment provides a delivery system and methods for the treatment of asthma or COPD. The drug-delivery system and methods may deliver asthma or COPD drugs by using both passive and active targeting. A method for treating asthma or COPD includes administering a delivery system including a nanoparticle with one or more drug that is an asthma or COPD therapeutic agent to a patient. The delivery system employed in the methods of treating asthma or COPD may include one or more targeting agent specific for asthma or COPD treatment on a nanoparticle including the one or more drug that is an asthma or COPD therapeutic agent.

As mentioned, a lung-specific delivery system may employ both passive and active targeting to intravenously deliver anti-cancer drugs to tumor cells. The first layer of the delivery system is a gel microparticle designed to take advantage of the venous lung filtration pathway and passively accumulate in the lungs after intravenous injection into the body. The GMP may be composed of crosslinked, functionalized biocompatible polymers including but not limited to poly(2-hydroxyethyl methacrylate), dextrans, polyphosphates, poly(lactides), poly(glycolides) and polyethylene glycol (PEG) based polymers. Degradable linkages between the gel crosslinks can be incorporated to control the release rate of the NPs. The degradable linkages can include but are not limited to esters, succinates and diglycolates. The size of the GMPs may vary depending on the gel composition, but may be in the micron range.

In an embodiment, the GMPs have a size in the range from 1 to 100 µm. The GMPs may have a size of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 µm. The GMPs may have a size in a range between and including any two integer µm sizes selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 µm. As a non-limiting example, the GMPs may have a size in the range between and including 6 µm and 7 µm. As another non-limiting example, the GMPs may have a size in the range between and including 6 µm and 20 µm. The deformability of the particles may be considered when choosing the size of the GMPs. In an embodiment, the GMPs are biocompatible and safe.

A second layer of a delivery system may include one or more types of nanoparticles (NP) embedded in the GMP. In an embodiment, the second layer of the delivery system include two types of nanoparticles (NP) embedded in the GMP.

The NP surfaces may be decorated with ligands to actively target cells. A targeting approach is to decorate the surface of the NP with one or more ligands that bind to specific cell receptors. A wide variety of ligands can be used as targeting agents herein. In an embodiment, a targeting agent is selected from ligands that bind overexpressed or uniquely expressed receptors on the surface of the target cells. The field of receptors is reviewed in references 1-32, which are incorporated herein by reference as if fully set forth. A ligand may be chosen as a targeting agent from ligands that bind a receptor described in references 1-32.

In an embodiment, the release rate of the NPs from the GMPs into the tumor and the release rate of the anti-cancer drug from the NPs can be tuned to achieve a desired effect. The GMP mesh size and degradation rate may control the release of the NPs.

The deformability, or stiffness, of the gel particle can be tuned to optimize retention at the desired site. The combination of stiffness and size may affect retention and clearance.

An embodiment includes a method including administering a delivery system herein. The delivery system could also be adapted for injection (e.g., intravenous injection) so that the GMPs accumulate in the lung capillaries and release the NPs. The delivery system could also be adapted for injection (e.g., arterial injection) close to the kidney so that the GMPs accumulate in the kidney and release the NPs. The delivery system could also be adapted for injection (e.g., arterial injection) close to tumor sites in the body so that the GMPs accumulate in the tumor vasculature and release the NPs. The therapeutic agents may be selected based on the site where the delivery system will be filtered or stopped. The targeting agents could be selected based on the site where the delivery system will be filtered or stopped. The chemopotentiator could be selected based on the site where the delivery system will be filtered or stopped.

In an embodiment, a method of making the delivery system includes two steps. The first is the synthesis of drug loaded NPs. The NPs loaded with hydrophobic drugs can be made using Flash Nanoprecipitation (FNP). A FNP technique that may be utilized is described in references 33-35, which are incorporated herein by reference as if fully set forth. In FNP, an agent; e.g., an anti-cancer drug, can be encapsulated in the core of a block-copolymer based NP and released over time. The copy number and density of targeting ligands on the surface of an NP can be controlled by the concentration of functionalized block-copolymers and the type of linkage between the block-copolymer and the ligand.

Referring to FIGS. 7(a), (b), (c) and (d), to controllably create GMPs of a selected size and NP loading, microfluidic devices with flow focusing capabilities may be employed. In flow focusing microfluidic devices, an outer sheath flow 710 stretches the inner liquid filament 720 and causes the breakup of the liquid into droplets. Functionalized polymers; e.g., PEGs with degradable linkages, NPs, crosslinking initiator and solvent are mixed to form the inner liquid filament and a hydrophobic fluid is used to make the sheath fluid. Once the droplets have been formed, they are crosslinked to create the GMP.

To produce GMPs on a commercial scale, emulsification techniques can be employed to make GMPs loaded with NPs. To create an emulsion, the aqueous soluble polymer with degradable linkages, NPs, crosslinking initiator and solvent are mixed and then introduced into a hydrophobic fluid phase. The aqueous solvent will form the discontinuous phase, while the hydrophobic fluid will form the continuous phase of the emulsion. The energy input controls the size of the droplets in the emulsion and hence the size of the GMPs. Once the emulsion is made, the droplets are crosslinked to create the GMPs. An effect of adding NPs to the aqueous phase, which will be polymerized to form the GMP, may be to increase the fluid phase viscosity and therefore increase emulsion drop size. The drop size may approximately correspond to the drop size that would be generated from a fluid with the continuous viscosity equal to that of the dispersion.

In an embodiment, the droplets of aqueous phase containing the polymer, drugs, and NPs can be produced by emulsification processes that are widely known by those in the art. Appropriate processes are described in reference 36-38, which are incorporated herein by reference as if fully set forth.

The droplets in the emulsion phase can be gelled using a variety of chemistries. These include but are not limited to free radical polymerization, mannich (i.e., thio-vinyl) reactions, hydrophobic association, metal ion mediated complexation, amide formation reactions, ester formation reactions, and azide alkyne Huisgen cycloaddition.

The radical reactions can be initiated with a variety of methods including but not limited to using UV light and photoinitiators, temperature, or redox initiation.

In an embodiment, the delivery system aims to overcome toxicity by selectively targeting the lung to deliver anti-cancer drugs or anti-TB drugs such that systemic exposure is avoided. Similarly GMP particles can be targeted to the liver for the delivery of drugs; e.g., anti-cancer drugs. The GMP-NP delivery can be adapted to deliver other drugs selectively to the lungs including but not limited to asthma, COPD, and tuberculosis drugs. IV administration of the GMP-NP system may allow for the delivery of drugs into the deep lung.

Embodiments include methods employing an intravenously (IV) administered lung-targeted nanoparticle (NP)/gel microparticle (GMP) delivery system for the treatment of disease. Two levels of targeting may be achieved. The first level is passive targeting. GMPs selectively accumulate in the lung or liver after IV administration. Data herein demonstrates that passive targeting may achieve a 10-fold increase in anti-cancer drug potency and 10-fold lower peak systemic drug concentrations. The second level is active targeting. Different types of NPs may be provided to achieve active targeting. High drug loading into NPs may be achieved using a fabrication process described below that overcomes the solubility limits of hydrophobic cancer drugs. NP surfaces may be functionalized with ligands that selectively target cancer cells or macrophages for TB therapy. An NP may be functionalized with cell surface ligands. These NPs could be engineered to tightly bind to cell surface receptors and remain there. Once the GMPs passively accumulate in the lung or liver, the NPs imbedded in the GMP matrix may diffuse out and seek targets, which may be cancer cells. The targeting approach may result in specificity of treatment and an additional 10-fold reduction in effective drug concentrations.

Embodiments including a targeting approach for a delivery system or method may be significant for two reasons. First, they may achieve effective lung or liver drug concentrations while minimizing systemic exposure and toxicity in healthy tissues. Treatment options that reduce the duration of platinum-based cancer chemotherapy while improving quality of life and progression-free survival are considered a high priority, The first level of targeting (i.e., passive) to target tissue can be included to reduce or avoid the injection of free NPs, which could lead to widespread body distribution and extravasation into non target tissues. Passive accumulation may deposit GMPs directly into the lung or liver and limit total body distribution of drug-bearing NPs. This can be useful if there is a lack of complete ligand-receptor specificity and a distribution of receptors in organs other than the target organ. A multifunctional delivery system and methods herein may provide highly efficient lung or liver targeting in order to achieve local sustained drug concentrations and minimal systemic exposure to maximize therapeutic efficacy while minimizing side effects. The systems and methods herein may also be used to provide a platinum-free drug regimen.

The lung is the only organ in the body that accepts the entire venous blood output from the heart. Since it is the first capillary bed encountered by the venous blood, it is in a singular position to entrap a wide variety of particles. "Passive" drug targeting to the lung (i.e., accumulation) can be achieved by taking advantage of this natural flow-filtration phenomenon. Human serum albumin macroaggregates (MAA) and MPs are efficiently entrapped (>90%) after a single injection as compared to only 5-20% of an inhaled dose. Inhalers often must be used multiple times daily but a single IV injection may provide effective treatment for longer periods. For example, a single IV injection may provide effective treatment for up to one week. Size and deformability are the two major determinants of the passive accumulation and retention of MPs in the lung.

In an embodiment, chemopotentiators may be delivered in conjunction with the delivery system. The chemopotentiators may be included in the delivery system or separately. The chemopotentiators may be included on or in the nanoparticles. The chemopotentiators may include one or more of 3-aminobenzamide, misonidazole, 3-bromopyruvate, nitracrine, dipyridamole, hydralazine, amonafide, PSK (krestin), DPPE (tesmillifene), homoharringtonine, quinamed, NOV-002, or ABT-737.

The delivery systems and methods herein may include a pharmaceutically acceptable salt, solvate or derivative of a drug or targeting agent. Pharmaceutically acceptable salts that may be included in embodiments herein can be found in Handbook of Pharmaceutical Salts: Properties, Selection, and Use, Stahl and Wermuth (Eds.), VHCA, Verlag Helvetica Chimica Acta (Zurich, Switzerland) and WILEY-VCH (Weinheim, Federal Republic of Germany); ISBN: 3-906390-26-8, which is incorporated herein by reference as if fully set forth.

The delivery systems and methods herein may include pharmaceutically acceptable carriers, which may be selected from but are not limited to those in the following list: ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts or electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, talc, magnesium carbonate, kaolin, non-ionic surfactants, edible oils, physiological saline, bacteriostatic water, Cremophor EL™ (BASF, Parsippany, N.J.) and phosphate buffered saline (PBS).

Any single embodiment herein may be supplemented with one or more element from any one or more other embodiment herein.

EXAMPLES

The following non-limiting examples are provided to illustrate particular embodiments. The embodiments throughout may be supplemented with one or more detail from any one or more example below. The following examples do not limit the claimed invention to the particular features described.

Example 1

Figure 2:
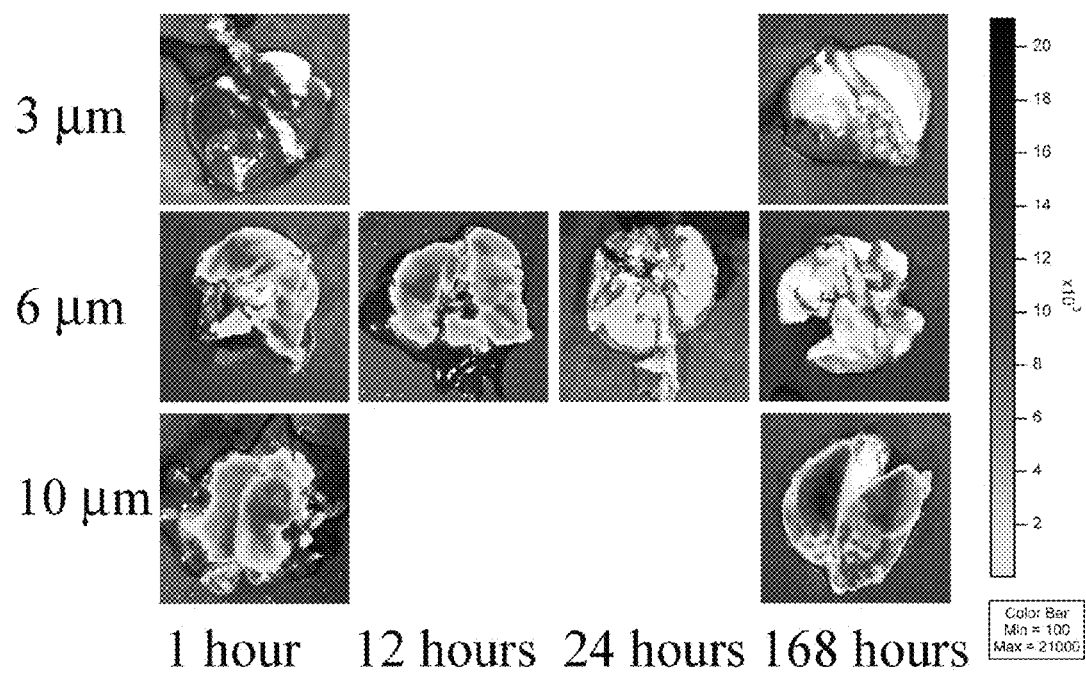
FIG. 2 illustrates passive lung accumulation of IV injected 3, 6 and 10 µm fluorescently labeled polystyrene MPs in healthy rats.

Engineering and Evaluation of a Series of GMPs to Achieve (a) Passive Lung Targeting Efficiency, Retention and Elimination and (b) Lower Pulmonary Toxicity (Structural and Functional Alterations and Inflammation) in Normal Mice and in an Orthotopic Mouse Model of Lung Cancer Optimal threshold size for passive pulmonary targeting and retention of rigid MPs is ~6 µm. Referring to FIG. 2, rigid internally labeled fluorescent polystyrene MPs of various sizes (2, 3, 6 and 10 µm) were administered IV to male Sprague Dawley rats. Total lung retention, biodistribution and intra-lung distribution were assessed using either a fluorescent plate reader or a Xenogen IVIS 100 Imaging System (IVIS, Caliper Life Sciences, Hopkinton, Mass.). As shown in FIG. 1, targeting was highly efficient (>95%) but retention was size dependent. No acute toxicity was observed. Complete entrapment and retention of 10 µm MPs was observed for the one-week duration of the study, whereas 2 µm and 3 µm MPs readily passed through the lung. 80% of the 6 µm. MPs were retained for the first 2 d with 15% being slowly cleared over the next 5 d suggesting a possible threshold size for rigid MPs (FIG. 1). Six µm and 10 µm MPs were widely distributed throughout lung tissue with evidence of entrapment in pulmonary capillaries but not arterioles. Based on these results, rigid 6 µm MPs transiently but efficiently target the pulmonary capillaries. Systemic administration of MPs may be an efficient alternative to inhalation for delivery to the lungs. In some embodiments, passive pulmonary targeting may offer two advantages over inhalation: (1) higher localization efficiency (e.g., 95% vs ~15% as shown in this example) and (2) wide distribution and penetration into the deep lung. See reference 39, which is incorporated herein by reference as if fully set forth.

Figures 2A, 2B:
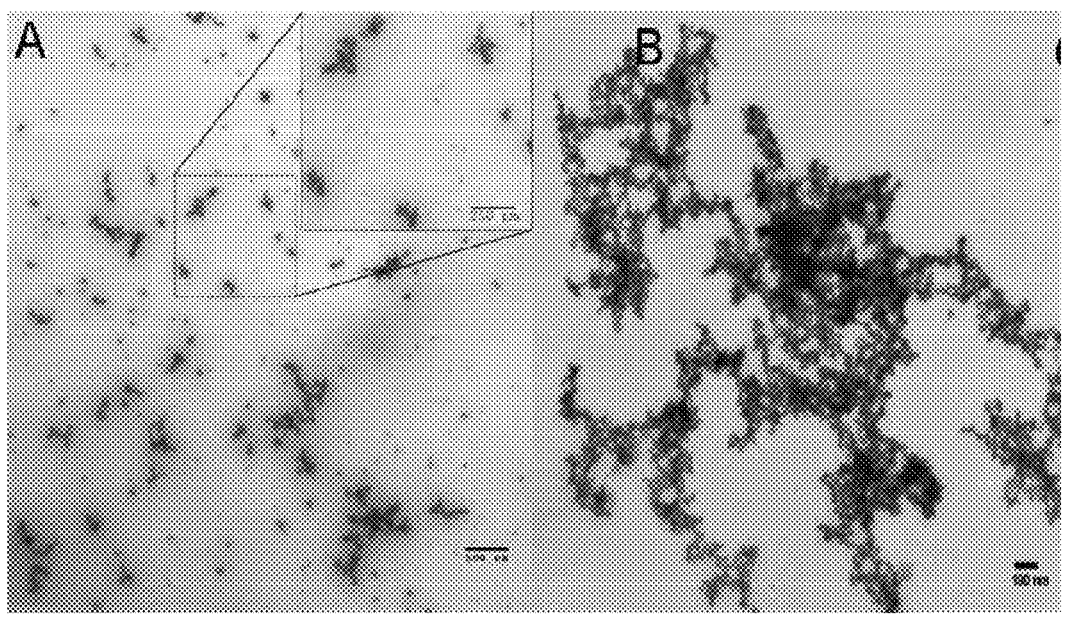
FIG. 2(a) illustrates TEMs of PEG nanogels.
FIG. 2(b) illustrates micron-sized aggregated nanogel particles (ANPs).
Figure 3:
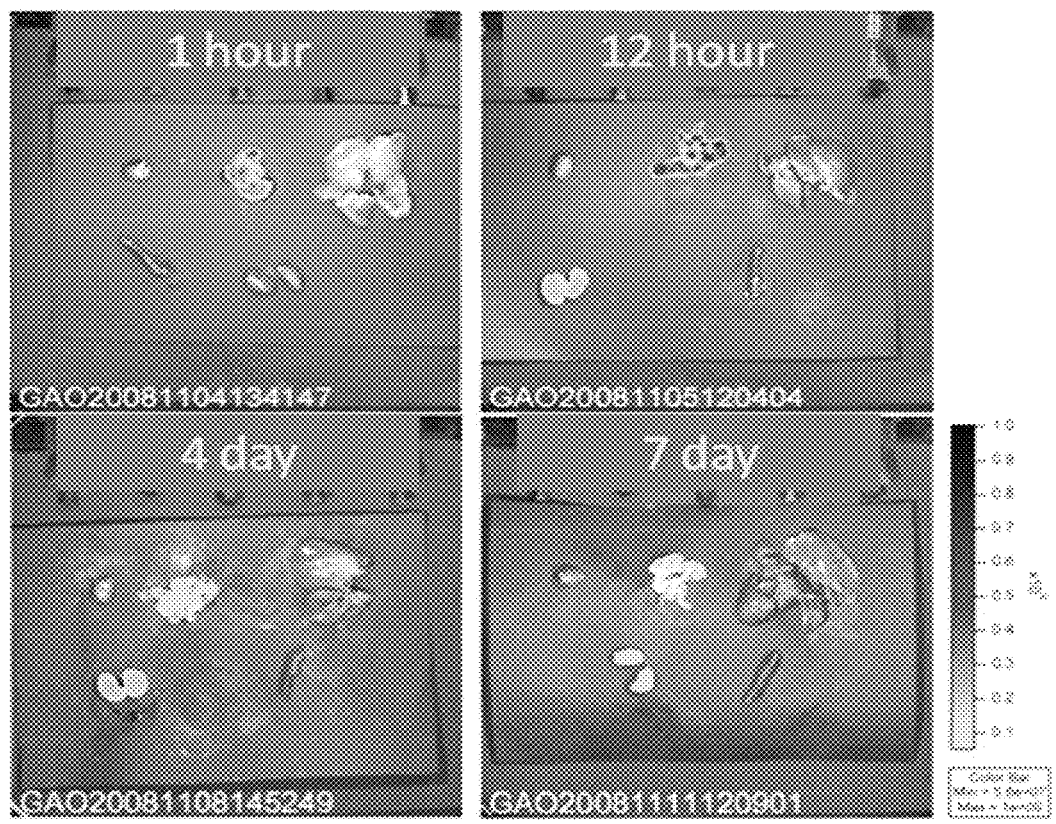
FIG. 3 illustrates ANP accumulation in rats.

The size threshold for passive pulmonary targeting of some highly deformable MPs is ~30 µm. The passive lung targeting and retention of highly deformable, micron-sized aggregated nanogel particles (ANP) were investigated. Referring to FIGS. 2(a) and (b), PEG nanogels (~20 nm) were prepared using a 20 kDa 8-arm PEG-SH nanocarrier crosslinked using a 1,6-hexane-bis-vinylsulfone (HVBS) at various stoichiometries (1:1, 0.5:1, and 0.8:1). FIGS. 2(a) and (b) shows typical transmission electron microscopy (TEM) images of nanogels (FIG. 2(a)) and ANPs in the low micron size range (FIG. 2(b)) that were negatively stained using aqueous solution of 0.5% uranyl acetate. As the ANPs self-assemble, they take on a more flexible spider-like shape similar to that reported for the commercial MAA lung perfusion diagnostic MPs. Referring to FIG. c-3, biodistribution studies of ANPs covalently labeled with HiLyte750 dye (DYE-ANPs) were performed. ANPs of three sizes were prepared (10-30, 30-50 and 50-60 µm). 55 µm DYE-ANPs (mg/kg) were administered (16 mg/kg) to male Sprague-Dawley rats by tail vein injection. Biodistribution of ANPs was determined using an in vivo imaging system (IVIS). Using IVIS, ANP peak accumulation was found to occur between 6-12 hrs. Peak ANP accumulation was found to occur between 6-12 hr. ANPs were retained in the lungs in high concentrations for 4-5 days with detectable amounts through the 7 days of the study. Larger ANPs (50-60 µm) preferentially accumulated in the lung within 30 min with the majority remaining in the lung for more than 7 days (FIG. c-3). Although smaller ANPs (10-30 µm) also accumulated in the lung with high efficiency, the overall residence time was approximately one week with a reduced signal after about 3-4 days (not shown). Intermediate results were observed for medium sized ANPs (30-50 µm). Toxicity was not observed at any of the doses administered (not shown). Based on these results, the lung targeting efficiency of all 3 sizes of ANPs studied was high (>95%) while lung retention varied according to size. ANPs in the 30 µm range may have better lung retention. Highly deformable MPs may be larger than rigid MPs in order to be retained in the lung for a one week time span.

Figure 4:
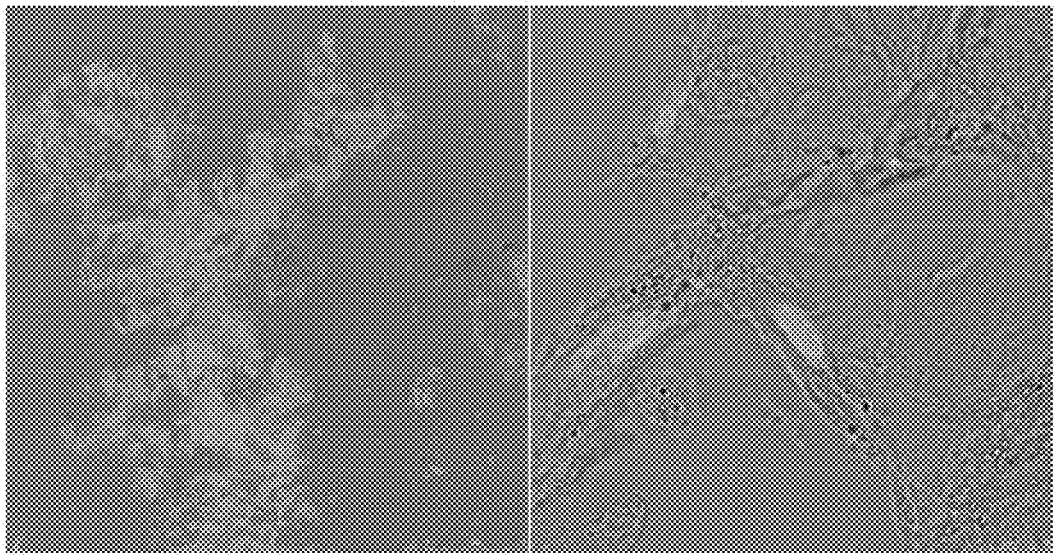
FIG. 4 illustrates fluorescently labeled ANPs localized in pulmonary capillaries.
Figure 5:
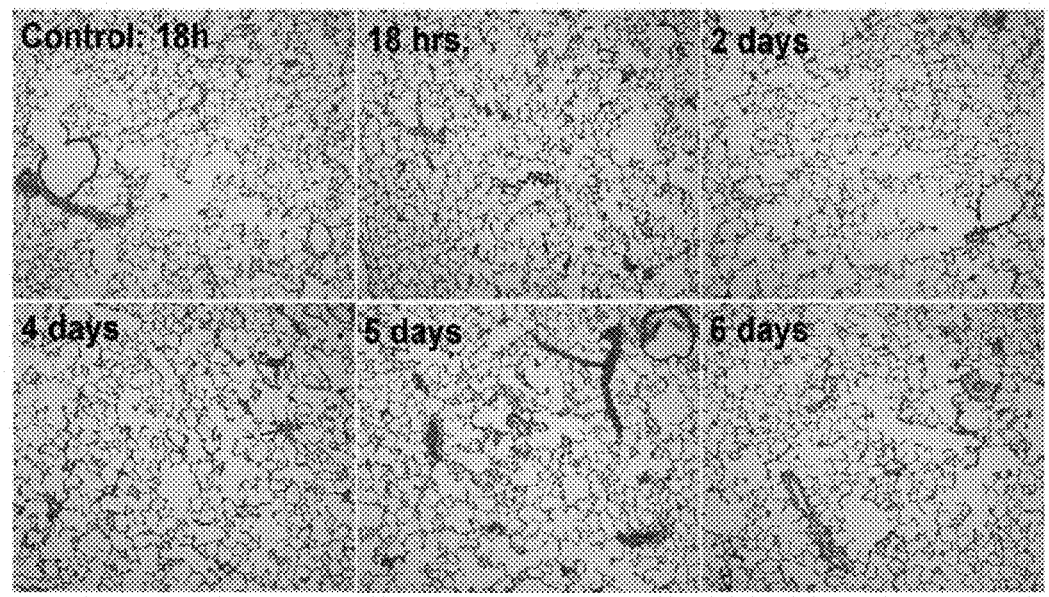
FIG. 5 illustrates lung histology following ANP injection.

ANPs do not appear to be toxic at large particle doses (16 mg/kg) in rats. Histologic sections of lungs from rats treated with ANPs were assessed for evidence of toxicity. Referring to FIG. 4, fluorescent labeled ANPs (left panel) were injected IV (16 mg/kg) into rats. Sections of lung were prepared 7 days later and analyzed by confocal microscopy. Note the accumulation of ANPs in the lung capillaries (right panel). FIG. 4 shows fluorescently labeled ANPs localized in pulmonary capillaries. Referring to FIG. 5, lung histology following ANP (20 µm) injection is illustrated. Lung samples were collected at 18 h to 6 days post particle injection, embedded in paraffin and sections stained with H & E. (Magnification 100×). No significant structural alterations were noted in the lung. These results demonstrate that large doses of poly(ethylene glycol) ANPs do not appear to be cytotoxic (FIG. 5).

Figure 6:
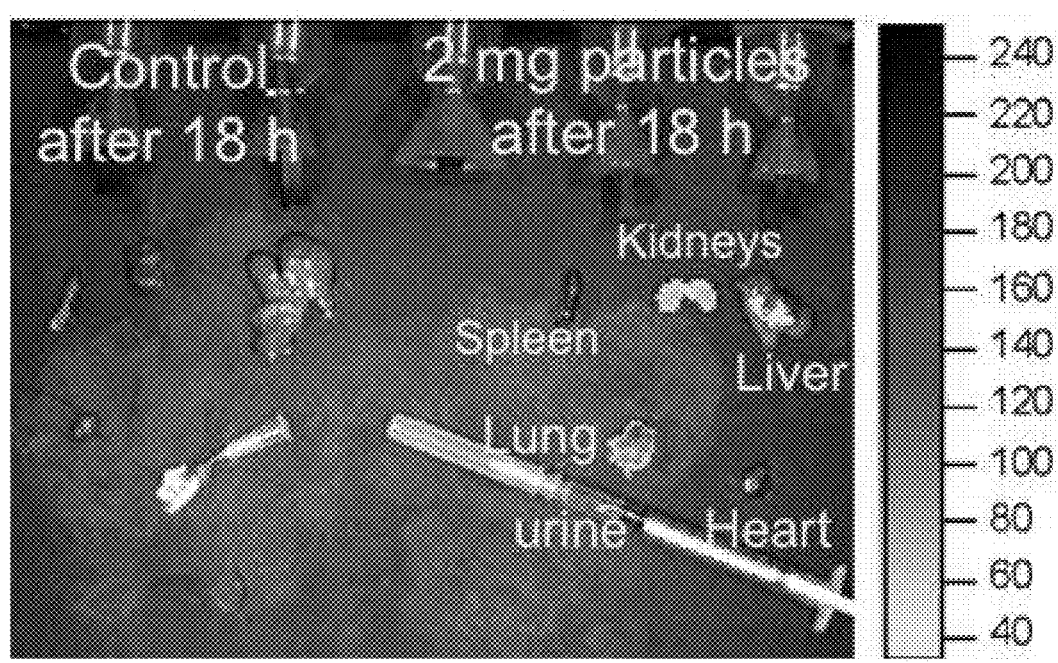
FIG. 6 illustrates ANP accumulation in mice.

Species independence of MP lung accumulation. Referring to FIG. 6, biodistribution studies of ANPs covalently labeled with HiLyte750 dye (DYE-ANPs) were performed. FIG. 6 shows lung accumulation of 25 µm ANPs in mice 18 h after N injection of 1 mg of ANPs. 200 µL PBS (control) or DYE-ANPs (Dose: 1 mg in 200 µL PBS, Particle size: 25 µm) were administered intravenously to BALB/C mice. Biodistribution of DYE-ANPs was determined using IVIS. DYE-ANPs were found to accumulate in the lung with the same pattern as rats. Lung accumulation and retention pattern was similar to results in rats for similarly sized ANPs. These results are consistent with literature showing that there is not a major difference between species and their MP accumulation patterns in the lung. See references 40 and 41, which are incorporated herein by reference as if fully set forth.

Figure 7:
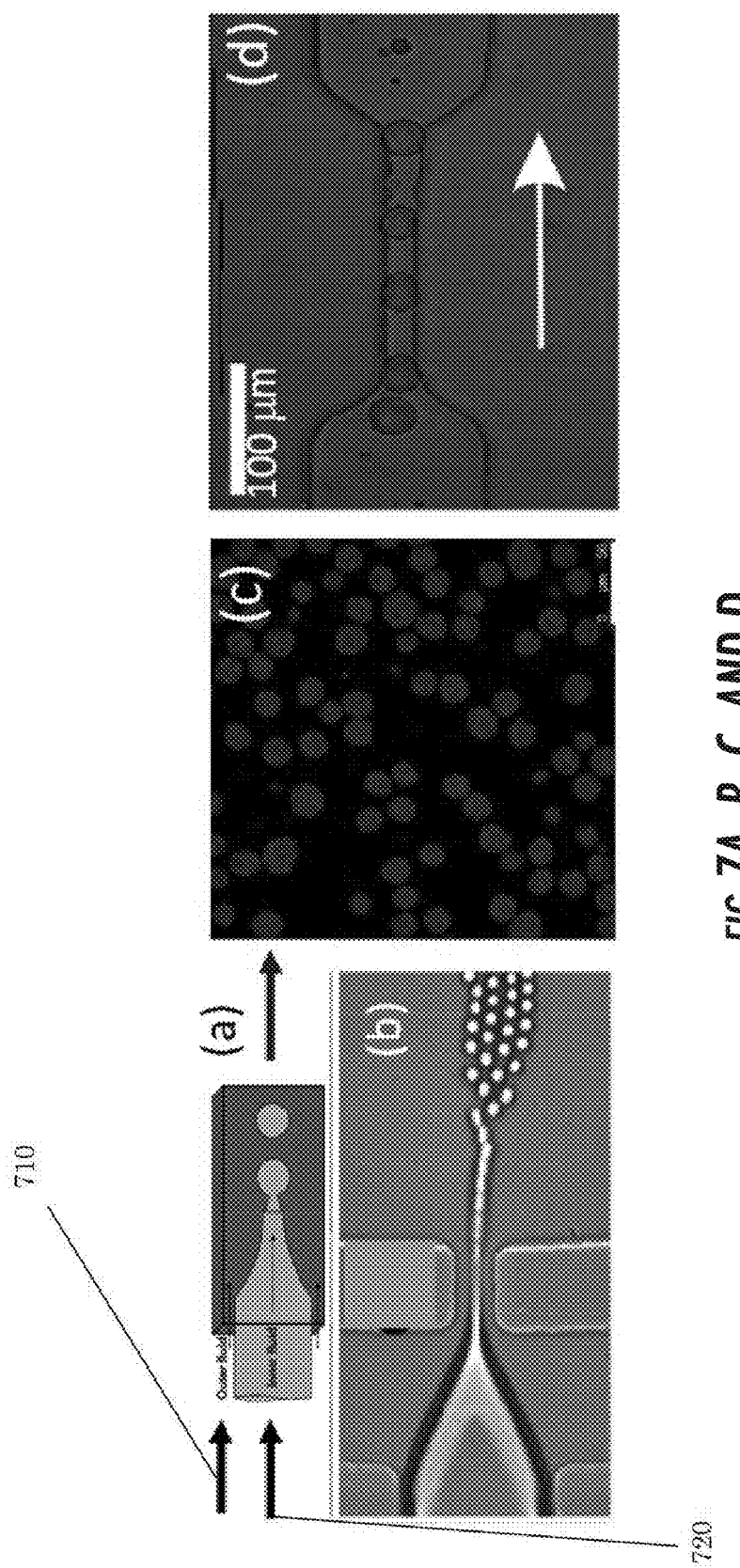
FIG. 7(a) illustrates a schematic of flow focusing geometry where the outer sheath flow stretches and breaks the drops into a uniform size.
FIG. 7(b) illustrates images of drop breakup for flow through a 43.5 µm orifice with a ratio of inner to outer flow rates of Qi/Qo=1/40.
FIG. 7(c) illustrates PEG polymerized GMPs with an average size of 8 µm containing 100 nm NPs containing fluorescent dye showing the successful production of NPs encapsulated in GMPs.
FIG. 7(d) illustrates a time-lapse image of PEG polymerized 25 µm GMPs being forced through a 20 µm contraction as a model of capture in the lung capillaries.

Microparticles (MPs or GMPs) of precisely tailored sizes and tailored deformabilities can be fabricated using microfluidics. Microfluidics (MF) is the rapidly developing field of using flow geometries at the micron scale to enable control of chemical reactions (see references 42-46, which are incorporated herein by reference as if fully set forth), crystallization (see references 43-46, which are incorporated herein by reference as if fully set forth), diagnostics (see references 47-51, which are incorporated herein by reference as if fully set forth) and particle formation (see references 33 and 52-60, which are incorporated herein by reference as if fully set forth). Conditions to break fluid streams into uniform micron-sized droplets can be found in reference 53, which is incorporated herein by reference as if fully set forth. Small, uniform drops can be made by techniques involving "flow focusing" (see references 52, 53 and 50, which are incorporated herein by reference as if fully set forth) in which an outer sheath flow stretches the fluid filament and causes breakup as shown schematically in FIGS. 7 (a) and (b). These figures show an image of 6 µm drops being produced by flow focusing. Microfluidic technologies provide an ability to fabricate GMPs of controlled softness or deformability. The GMPs made to validate the approach are shown in FIG. 7(c). The sheath fluid included polydimethylsiloxane (PDMS) (Dow Corning Corporation 749® fluid, Aldrich) containing ~2.0 wt. % initiator (2-hydroxy-4'-(2-hydroxyethoxy)-2-methylpropiophenone). For the gel phase, an aqueous solution of 75 vol. % PEG diacrylate macromer (Sartomer, SR259), 0.07 wt. % initiator and 2.0 wt. % SDS was used. 100 nm NPs containing red fluorescent dye (Ciba, Hostasol red) were incorporated (1% wt. of NPs) to produce the brightly fluorescent ~10 µm droplets (FIG. 7(c)). The GMP gel phase encapsulates the NPs containing the fluorescent dye. The microfluidic chips were prepared using standard methods of soft lithography. Prior to injection, the microfluidic chips were treated with octadecyltrichlorosilane (OTS) to make the glass surface hydrophobic. Flow rates of the oil and aqueous phases were adjusted to achieve a monodisperse suspension of water droplets with the desired size (diameter: ~10 µm) suspended in the oil phase. Droplets were collected in three vials and the vials were exposed under a longwave UV lamp (Ultra-Violet Products Inc., Blak-Ray®) for different times (1, 3, and 9 min), which adjusts the degree of cross-linking and ultimately GMP softness (i.e., shear modulus G). The modulus can be varied by changing: (1) molecular weight of the PEG macromer where decreasing the Mw from 3000 to 200 will increase the modulus by 60 fold (see reference 61, which is incorporated herein by reference as if fully set forth), (2) the macromer concentration (e.g., moduli may increase from 60 to 500 kPa as the concentration of 3000 Mw PEG increases from 10 to 20%. See references 62-63, which are incorporated herein by reference as if fully set forth), (3) extent of reaction by varying the UV exposure time, and (4) ratio of linear, 4 arm and 8 arm PEG macromers. Hydrogel formation may be performed with 8 arm PEGs. Branched PEGs may create gels with substantially higher modulus than corresponding linear PEGs. See references 64 and 65, which are incorporated herein by reference as if fully set forth. Mixtures of one or more of 8 arm, 4 arm and linear PEGs can be used to tune modulus. The combined factors may enable varying the modulus by at least three orders of magnitude. A time-lapse photograph of a GMP entering a constriction is shown in FIG. 7(d). This provides a method of qualitatively assessing stiffness since constrictions of sizes from 4-20 µm can be made and the entry or trapping of the GMPs in the constriction can be visualized. The correspondence between in vitro to in vivo accumulation can be determined. Quantitative determination of GMP stiffness can be made by measuring the modulus of gel slabs of the same composition as GMPs using an Anton Paar MCR500 rheometer in a parallel plate geometry as done in reference 66, which is incorporated herein as if fully set forth. The modulus of the gel GMP may be defined as the modulus of a gel disk made from the same composition as the emulsion or microfluidics droplets with a thickness of 1 mm and diameter of 20 mm that is polymerized or gelled under the same polymerization conditions as the emulsion. The rheological measurement of the shear modulus of the gel disk under a strain of 0.1% may be defined as the modulus of the gel GMP. Uniform GMPs in the size range of 2-50 μm can be produced by microfluidics and fluorescent 100 nm NPs can be encapsulated in the GMP polymer network through the process.

Size and deformability are two determinants of MP passive lung accumulation and retention (see references 39 and 67-71, which are incorporated herein by reference as if fully set forth). A larger sized deformable GMP may have the same lung targeting properties as a smaller rigid MP. For each type of deformable GMP, a range of sizes can be produced. Passive lung targeting can then be assessed in normal mice for each GMP type in order to determine the optimal size for a fixed level of deformability. Toxicology and lung function can be investigated for an optimally sized GMP at each level of deformability. GMP lung retention time can be optimized by engineering the degradation rate of the MP matrix. As GMPs spontaneously degrade, their size may be reduced to a critical value allowing clearance from the lungs. Lung targeting and retention can be assessed in a mouse orthotopic lung cancer model as a function of cancer stage (early versus late). A non-limiting example of targeting, retention and toxicity that may be achieved includes >~90% passive targeting, ~7 day retention in lungs, and no acute toxicity or significant reduction of lung function due to GMPs.

Synthesis of degradable GMPs. GMPs can be formed by polymerizing functional PEG polymers with molecular weights below 200,000. In order to enable complete renal clearance of the biocompatible PEG building blocks upon GMP degradation PEG polymers or regions of PEG polymers less than 40,000 are preferred. The PEG-ester linkage used to make the PEG diacrylates can be tuned to provide a 20-fold change in hydrolysis kinetics using various diglycolate and succinate linkers (see reference 72, which is incorporated herein by reference as if fully set forth). A second degradation strategy employing PLA-PEG-PLA macromers to form hydrogels can be used (see reference 63, which is incorporated herein by reference as if fully set forth). The hydrolytically unstable polylactic acid (PLA) segments on the ends of PEG chains enhance and determine degradation rates. The synthesis of PLA-PEG block copolymers and the extension of tri-block architecture is provided in reference 73, which is incorporated herein by reference as if fully set forth. The lessons learned about optimum GMP size and modulus above could be the basis for synthesizing PEG macromers with appropriate degradable ester and PLA linkages to tune both the GMP clearance rate from the lungs and the NP release kinetics from the degrading GMP.

Orthotopic NSCLC Mouse Model. An orthotopic NSCLC mouse model can be based on an established rat model described in reference 74, which is incorporated herein by reference as if fully set forth. The mouse model may be used facilitate in vivo imaging components. Human A549 NSCLC cells can be co-transfected with Katushka (a far-red fluorescent protein) and luciferase to facilitate tumor detection by in vivo/ex vivo imaging and microscopy. Transfected A549 (106 cells in 0.05 ml of 0.5 mg/ml Matrigel) cells can be implanted through the thorax into the left lung parenchyma as reported references 75-76, which are incorporated herein by reference as if fully set forth).

Assessment of lung toxicity and function. GMP can be injected into CD-1 mice intravenously. Lung function can be measured using a Scireq Flexivent at 1 and 7 days after injection. Mice can be euthanized, and bronchoalveolar lavage (BAL) fluid collected and evaluated for biomarkers of lung injury, inflammation and oxidative stress, as previously described in references 77-79, which are incorporated herein by reference as if fully set forth. The lung can be subjected to histologic scoring for severity of injury, morphologic/structural changes, and inflammation (Molecular Pathology Core Facility/NIEHS center). The Scireq Flexivent provides information on respiratory system mechanics including total lung resistance (central airway resistance+peripheral lung resistance) and static compliance responses at baseline and in response to pharmacologic challenge.

Other Methods: GMP fabrication and characterization and lung targeting and retention studies can be performed as described above.

The release of the 100 nm NPs from the GMP matrix may occur as the crosslinking sites in the gel matrix degrade and the mesh or pore size of the gel increases. This may allow diffusion of the trapped NPs out of the GMP. If the PLA-PEG-PLA GMP matrix gives inadequate NP release kinetics then the Michaels addition reaction between a vinyl group and a thiol may be used to form an alternative degradable hydrogel network.

Example 2

Design, Fabrication, and Assessment of NPs and GMPs that Enhance the Pro-Apoptotic Effect of Camptothecin (CPT)

Actively targeted NPs can be developed that specifically deliver CPT and a chemopotentiator to lung cancer cells to exploit synergy in tumor cell apoptosis induced by these two chemotherapeutic agents. The goal is to minimize the chemopotentiator, CPT and GMP doses in order to minimize toxicity. As described below, improvised CPT pharmacodynamics may occur during chemopotentiator-induced caspase activation and GMP lung residence time windows, which may allow lower effective chemopotentiator, CPT and GMP doses.

Figure 8:
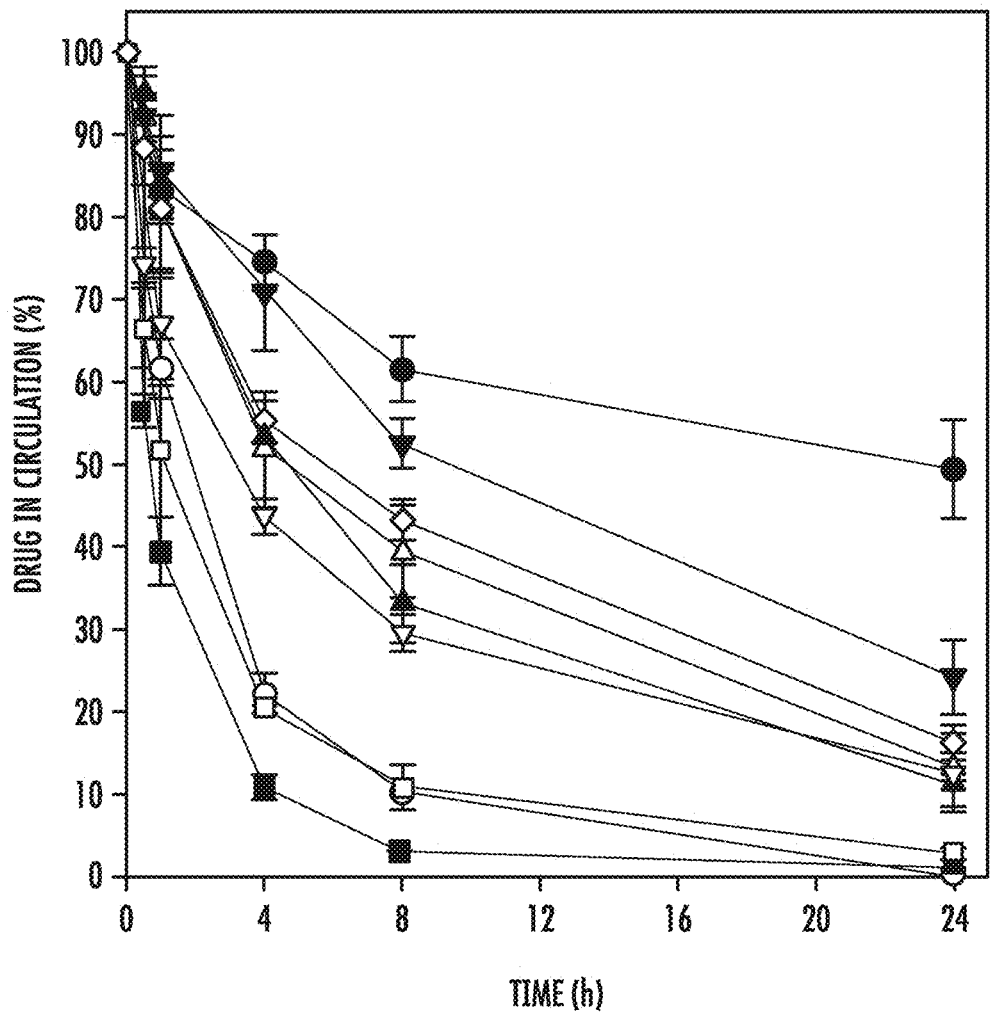
FIG. 8 illustrates paclitaxel release from 70 nm NPs in Foxn1$^{nu}$ mice.

Hydrophobic drugs such as CPT can be loaded into NPs and their release controlled using Flash Nanoprecipitation (FNP). A powerful technique using block-copolymer-directed assembly to prepare NPs from hydrophobic drugs at high loadings with narrow size distributions over the size range of 40-500 nm is described in references 33-35 and 80-81, which are incorporated herein by reference as if fully set forth. Hydrophobic drugs and amphiphilic block copolymers were initially dissolved in a water-miscible organic solvent (THF, methanol, or DMSO). The solvent quality was then rapidly reduced by micromixing against water to produce supersaturations as high as 1000 that drive rapid precipitation of all hydrophobic components (e.g., the drug and the hydrophobic block of copolymer). The process may depend upon the (1) time to attain homogeneous mixing ($\tau_{mix}$), (2) time of solute nucleation and growth ($\tau_{ng}$), and (3) time of block copolymer self assembly ($\tau_{sa}$). In kinetically controlled assembly regimes at high supersaturations, NPs grow by diffusion-limited aggregation and incorporate the components stoichiometrically. Complex mixtures of multiple drugs, fluorophores (see references 33 and 80, which are incorporated by reference as if fully set forth), $Au^0$ colloids for X-ray imaging (see reference 33, which is incorporated by reference as if fully set forth) and magnetic colloids for MRI imaging (see reference 81, which is incorporated by reference as if fully set forth) can be prepared. NP drug release kinetics can be controlled using a prodrug conjugation strategy. For example, paclitaxel was conjugated to a hydrophobic "anchor" molecule to retain it in the NP core until the hydrolytically unstable ester, ketal or orthoester is cleaved (see reference 82, which is incorporated by reference as if fully set forth). By tuning the hydrolysis kinetics of the linker, paclitaxel release kinetics ($t_{1/2}$) could be tuned from 1 to 24 hours as shown in FIG. 8 (see reference 82, which is incorporated by reference as if fully set forth) for 70 nm NPs after IV tail injection in Foxn1$^{nu}$ mice. The figure shows the percentage of the injected drug still in circulation in the mice. The symbols in FIG. 8 refer to paclitaxel conjugated to: (●) tocopherol with succinic acid, (○) oleyl alcohol with succinic acid, (◇) tocopherol with diglycolic acid, (■) oleyl alcohol with diglycolic acid, (□) octadecanol with diglycolic acid, (▲) cosanol with diglycolic acid, (△) docosanol with diglycolic acid, (▼) cholesterol with diglycolic acid, and (▽) 1,2-dimyristoyl-sn-glycerol with diglycolic acid. The lipids were conjugated to the cross-linker by treatment with the corresponding cyclic anhydride, followed by condensation of the anchor-linker product with paclitaxel using diisopropylcarbodiimide (DIPC) in the presence of N,N-4-dimethylaminopyridine (DMAP). Succinic acid and diglycolic acid were used as the cross-linkers. The 3-oxa moiety of the latter was intended to increase the susceptibility of the 2'-acyl group of the cross-linker to hydrolysis relative to the succinate analogues.

FNP enables the formation of NPs that can incorporate both CPT and chemopotentiator into the same NP. The release kinetics of the active moieties can be tuned by selecting appropriate hydrophobic "anchors" and sacrificial conjugating linkages. Methods of loading of hydrophobic drugs into NP can be found in references 33, 80 and 82, which are incorporated by reference as if fully set forth.

Nanoparticle diffusion out of hydrogel matrices such as GNPs can be finely tuned. A secondary targeting aspect of embodiments of the delivery systems and methods may utilize NPs that are imbedded into the GMP matrix. Diffusion of NPs or dendrimers through polymeric gels depends upon (1) the size of the diffusing species relative to the mesh size of the gel (related to polymer concentration in the gel), (2) the fractal dimension of the diffusing species and (3) and the diffusion distance (in this case, the size of the GMP). NP diffusion out of the GMP matrix may be predicted from earlier measurements discussed above and the optimized GMP gel polymer concentration. Tests of these predictions can be conducted on PEG diacrylate gels, which do not show degradation over a 7-day period (i.e., the sustained release target). Fluorescence measurements of NP release from GMPs can be conducted. Methods of tuning diffusion of nanoparticles can be found in references 83 and 84, which are incorporated herein by reference as if fully set forth.

Copy number and density of active targeting ligands can be precisely controlled on the surface of NPs. Methods of producing NPs with PEG protective coatings where the ends of the PEGs are functionalized for targeting can be found in reference 85, which is incorporated herein by reference as if fully set forth. The ratio of neutral PEG to functionalized PEG can be controlled by the FNP process to control targeting ligand concentration. The reactivity of the NP surface was linearly proportional to the fraction of maleimide in the PEG brush, and the coupling of Bovine Serum Albumin (BSA) and LHRH peptides to the NPs for targeting has been demonstrated. Extremely dense ligand concentrations on NP surfaces can be created. The mobility of the ligand can be controlled by changing the structure of the linker. For example, for 30 nm NPs the number of PEG groups was ~60075. The maximum BSA density on the NPs was 69 BSA/NP. With the hydrodynamic radius of BSA of 3.7 nm, a maximum of 66 BSA molecules would fit on the surface of a 30 nm sphere. To avoid denaturation during solvent precipitation, sensitive molecules may be coupled after formation of the NPs. Folate, can be attached to the block copolymer prior to assembly using click chemistry. This is demonstrated with a LHRH ligand NP targeting to MS578T breast cancer cells in vitro in reference 33, which is incorporated herein by reference as if fully set forth. Using FNP, NPs can be created with cancer cell targeting functionality using peptide and nonpeptide ligands. Methods of creating NPs with FNP can be found in references 33-35, which are incorporated herein by reference as if fully set forth.

Figure 9:
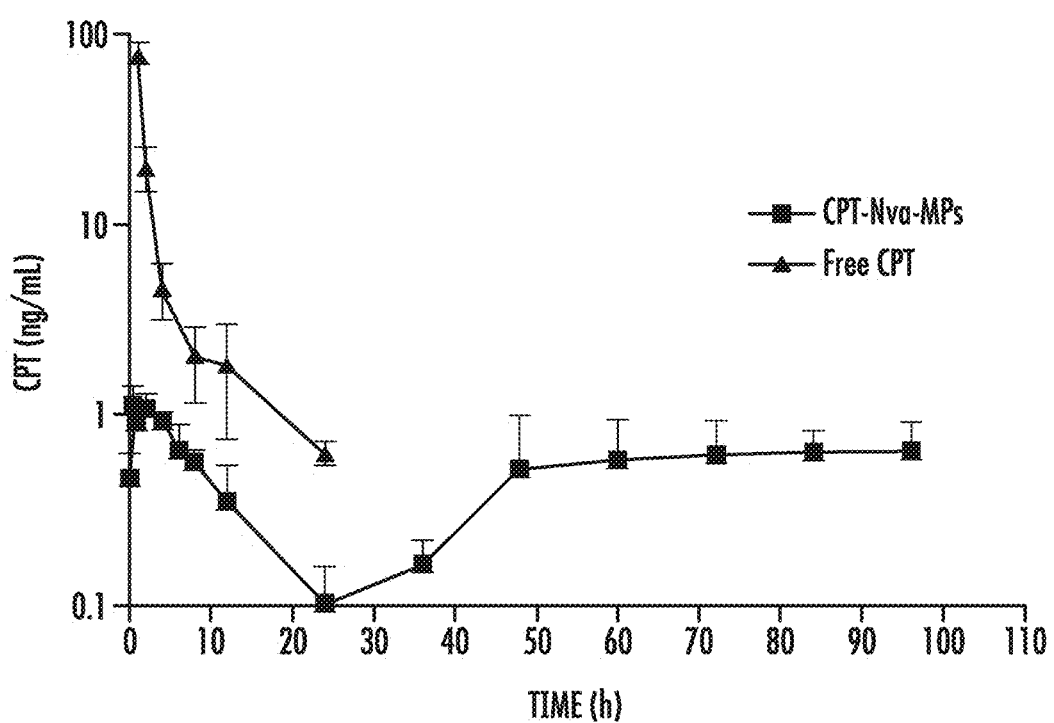
FIG. 9 illustrates systemic (plasma) concentration of camptothecin (CPT) as a function of time after a single bolus IV injection of CPT-Nva-MPs (CPT dose=0.2 mg/kg) (squares) and free CPT (2 mg/kg) (triangles). Values are reported as mean±SD. The lower limit of quantitation was 0.1 ng/mL. This indicates that systemic exposure of CPT after passive pulmonary delivery was near the LLOQ suggesting minimal systemic exposure/toxicity potential.
Figure 10:
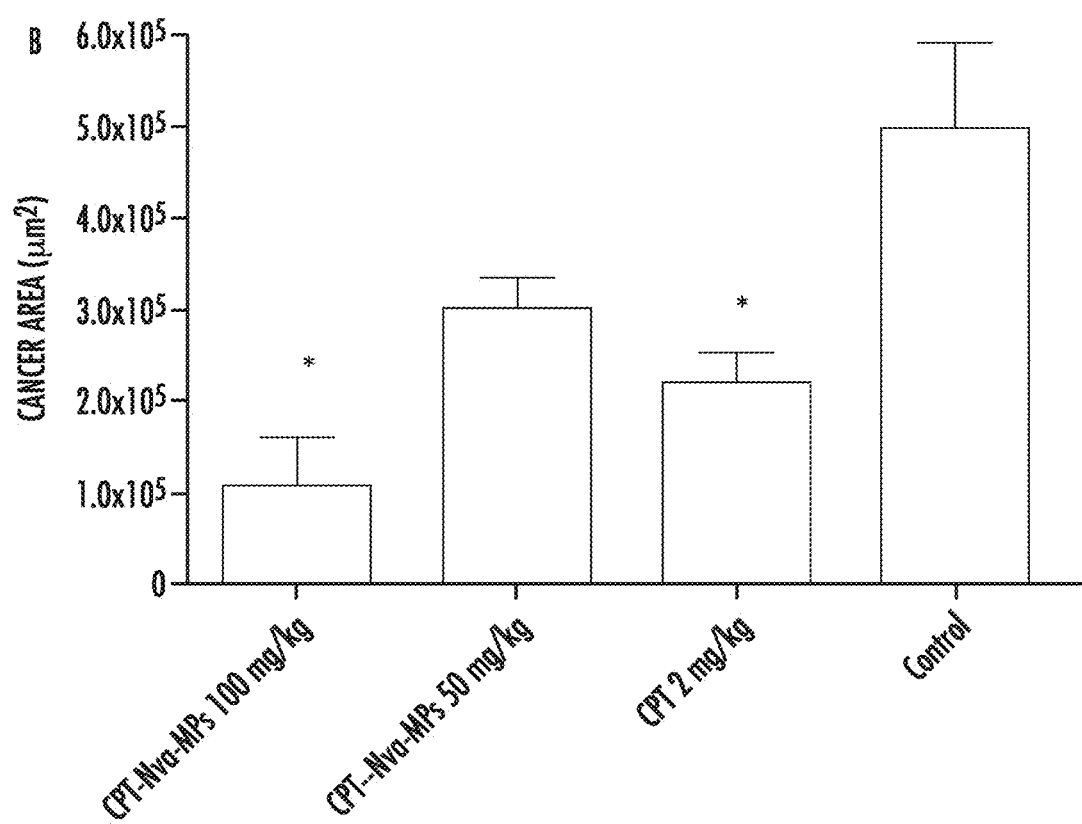
FIG. 10 illustrates a summary of the anti-cancer efficacy results the treatment groups (CPT-Nva-MPs (eq. CPT 0.2 mg/kg), CPT-Nva-MPs (eq. CPT 0.11 mg/kg), free CPT 2 mg/kg, and control (normal saline containing 0.1% TWEEN 80). Nude rats (n=5) were injected IV. The total area occupied by cancer cells in lung tissue (complete cross section) from rats receiving different treatments is represented on the Y-axis. Bars represent mean±SE (n=5). *=P<0.05 compared to control.

Passive pulmonary targeting of CPT using MPs increases in vivo potency/efficacy by ~10× and reduces the number of cancerous areas more significantly than IV injection of free CPT. PEGylated 6 μm polystyrene MPs with three copies of the norvaline (Nva) α-amino acid prodrug of CPT were prepared. Referring to FIG. 9, in vivo CPT plasma concentrations were low (~1 ng/mL or less) and constant over a period of 4 days after a single IV injection of CPT-Nva-MPs as compared to high but short-lived systemic exposures after an IV injection of free CPT. This suggests MP delivery achieved high local CPT concentrations in the lung. Referring to FIG. 10, anti-cancer efficacy was evaluated in an orthotopic rat lung cancer model and compared to a bolus injection of CPT. One week after A549 cell inoculation, nude rats were injected IV with CPT-Nva-MPs (50 and 100 mg/kg equivalent to CPT at 0.11 mg/kg and 0.22 mg/kg), free CPT (2 mg/kg) or vehicle control (saline containing 0.1% Tween 80). The treatment was conducted every 3 days for 27 days. The day after the last treatment, all animals were euthanized, and organs (lung, heart, liver, spleen and liver) were dissected and weighed. The organs were fixed in 10% neutral buffered formalin for H&E staining. Animals receiving either free CPT or CPT-Nva-MPs (0.2 mg/kg CPT) were found to have smaller areas of lung cancer (p<0.05, p<0.01, respectively) than untreated animals. In addition, 40% of the animals receiving CPT-Nva-MPs (0.22 mg/kg) were free of cancer. The passive pulmonary targeting of CPT: (1) resulted in exceptionally low systemic CPT exposure (equivalent to CPT blood levels after 7 elimination half-lives. To put this in perspective, a drug is considered to be eliminated from the body after 4-5 half-lives), (2) a significant reduction in cancerous areas in the lung, and (3) allowed for a 10-fold lower dose as compared to I.V. administration of free CPT. See references 74 and 86, which are incorporated herein by reference as if fully set forth.

Chemopotentiators. A battery of in vitro and in vivo studies, described below, may be used to assess chemopotentiation resulting in the calculation of the Dose Reduction Index (DRI) (See Statistical Design and Analysis, below). Unformulated drug and chemopotentiator can be studied in vitro (See Chemopotentiation Studies (In Vitro), below) to determine the Combination Index (CI) and DRI. Drug and chemopotentiator can be loaded into NPs at their optimal CI. In vivo studies can then be performed in an orthotopic mouse model (See Pharmacodynamic Studies (In Vivo), below). Since passive lung targeting alone resulted in >10-fold increase in the effective potency of CPT, an additional 10-100 fold increase in the effective potency of CPT may be gained using a chemopotentiator and actively targeted NPs.

Drug Rationale: A nanoplatform could be used to deliver numerous agents including but not limited to existing drugs, newly developed drugs, or a drug candidate that failed in clinical development due to toxicity, poor oral bioavailability, poor solubility in biological fluids, inappropriate pharmacokinetics, and lack of efficacy within a tolerable dose range. CPT16 (see references 87-99, which are incorporated by reference as if fully set forth) is a candidate. CPT16 is included in an embodiment of a delivery system and methods related thereto.

Some chemotherapeutic approaches ultimately elicit their effects via apoptosis, and manipulation at the level of apoptosis control may be a target of the systems and methods herein. Chemopotentiation may fulfill two functions: (1) it could selectively sensitize cancer cells to chemotherapy without effecting normal cells and (2) it could increase apoptotic drive.

Form Selection and Dose Rationale: Doses can be selected based on in vitro studies. For CPT: FNP can be used to encapsulate CPT into the NPs or it can be conjugated to the NP matrix in order to control release rate. If CPT forms with increased solubility are desired, CPT ester prodrugs (in particular, the norvaline prodrug) can be utilized (FIG. 10) (See reference 39, which is incorporated herein by reference as if fully set forth). For a chemopotentiator, any suitable form can be used. A hydrophobic version of an agent can be loaded into NPs using the FNP process, as described above. However, release rate can be further reduced. A mechanism to reduce release rates is to use calcium salts of an agent (e.g., a chemopotentiator) or conjugating the agent inside the NPs. If the chemopotentiator release rate needs to be increased, salt forms of the chemopotentiator dispersed in the GMP matrix could be used. GMP Dose: The target dose is estimated from FIG. 10 (see reference 39, which is incorporated herein by reference as if fully set forth). For a 250 g rat, 0.05 mg CPT may be used. This would require 0.13 mg NPs (using a paclitaxel loading of 38 wt. %). NP loading into the GMPs can be any amount. At 20%, viscosity of the GMP aqueous phase becomes a factor in administration or use of the delivery system. 40 wt. % or less GMP could be injected into the tail vein of mice. The initial GMP dose was ~0.5 mg. Using the synergy strategy described in this example, the GMP dose may be further reduced to 0.01 to 0.1 mg.

NP/GMP Preparation & Chemopotentiator/CPT Release Testing: GMPs could be fabricated using microfluidics and NPs loaded with CPT, Chemopotentiator or CPT/Chemopotentiator combinations using FNP as described above. The GMP "formulations" from Example 1 with optimal lung targeting, retention and toxicology properties can serve as a starting point. CPT/Chemopotentiator release can then be evaluated in vitro in mouse plasma and physiological buffers at pH 6.6, 7.0 and 7.4 corresponding to tumor, lung and extracellular fluid pH.

Chemopotentiation Studies (In Vitro): A549 cells can be cultured and passaged as previously described (see reference 39, which is incorporated by reference as if fully set forth). The free forms of CPT and chemopotentiator, and concentration-varying combinations thereof, can be evaluated in the assays described herein and combination effects can be determined as described by Chou (see references 102-104, which are incorporated by reference as if fully set forth). First, dose-response curves for CPT and chemopotentiator can be constructed and IC50s determined. Combination effects can be evaluated by combining both compounds at 0.25×, 0.5×, 1×, 2×, and 4× of their respective IC50s. Concentrations of CPT and chemopotentiator can range from 0-$10^6$ μM and treatment times could be 24, 48, 72, 96 hrs, 5 days, and 6 days, consistent with the studies above. Cell Viability Analysis, Caspase-3/7 and Caspase-9 and the DNA Fragmentation Assays may be conducted as describe in references 87 and 99, which are incorporated herein by reference as if fully set forth.

Pharmacodynamic Studies (In Vivo): GMPs containing CPT, chemopotentiator and CPT/chemopotentiator combinations at optimal cytotoxic ratios can be tested in the orthotopic NSCLC murine model. Negative controls can include solvent only and nontreated animals. Treatments can be started at 1 week after tumor injection, and repeated weekly for 3 weeks. Efficacy could be evaluated by examining the primary tumor, regional lymph node and distant metastasis including separate tumor nodule(s) in contralateral lobes. Tumor size could be monitored twice-weekly using bioluminescence and fluorescence whole body imaging (IVIS, Xenogen). After gross examination, various tissues (lung, regional lymph nodes, liver, spleen, kidney, lymphoid tissue, bone, blood, and brain) can be subjected to ex vivo imaging to further examine tumor distribution. The tissues can then be homogenized and analyzed by luninometry and fluorometry. Apoptosis can be examined by TUNEL assay as described in reference 99, which is incorporated herein by reference as if fully set forth. Vessel density in tumor could be assessed as described in reference 99, which is incorporated herein by reference as if fully set forth. Tissue samples could be embedded in paraffin, sectioned, and subjected to histopathological evaluation.

Statistical Design and Analysis: Compusyn 3.01 (Combosyn Inc, Paramus, N.J.) could be used to quantitatively analyze drug combination and dose-effect relationships as described by Chou (See references 105-107, which are incorporated herein by reference as if fully set forth). Data (e.g., dose-response of drug 1, drug 2, and drug 1+drug 2) can be used to construct median-effect plots using log [fa/(1−fa)]=mlogD−mlog($ID_{50}$), where fa is the fraction of system affected by dose D, $ID_{50}$ is median dose for tumor inhibition, and m is a Hill-type coefficient (m) signifying the sigmoidicity of the dose-effect curve. $ID_{50}$ values of individual drug 1, drug 2, and combination drug 1+drug 2 as well as m can be obtained from the plots. For a selected effect (x %), doses of drug 1 ($Dx^1$), drug 2 ($Dx^2$) and drug 1+drug 2 ($Dx^{1+2}$) needed to produce this effect could be calculated using Dx=$ID_{50}$[fa/(1−fa)]1/m. $Dx^{1+2}$ could be further dissected into dose fractions of drug 1 [$(D)_1$] and drug 2 [$(D)_2$] by equations $(D)_1$=$Dx^{1+2}$×P/(P+Q) and $(D)_2$=$Dx^{1+2}$×Q/(P+Q), where P:Q is molar ratio of drug 1:drug 2. Combination index (CI): CI=$(D)_1$/$Dx^1$+$(D)_2$/$Dx^2$. CI<1, =1 and >1 represent synergistic, additive and antagonistic effects, respectively. Dose-reduction index (DRI): represents the fold reduction in drug dose at a given effect level compared to individual drug doses. $DRI_1$=$Dx^1$/$(D)_1$.

Figure 11:
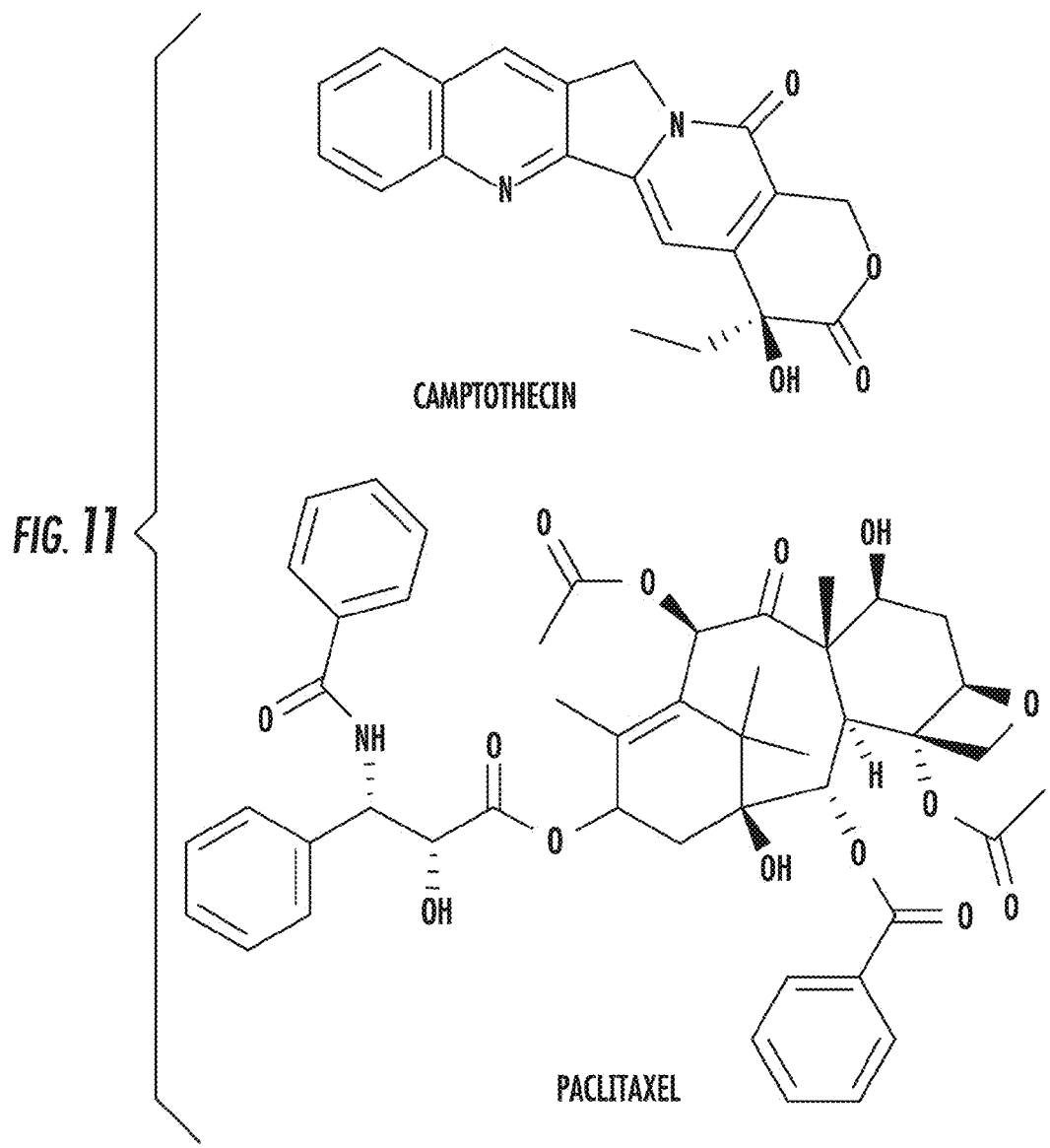
FIG. 11 illustrates structures of exemplary lung cancer drugs and compounds that could be encapsulated and included in a gel microparticle construct.

A variety of drugs can be used in embodiments herein and these include but are not limited to paclitaxel, etoposide topotecan, -aminobenzamide, misonidazole, 3-bromopyruvate, nitracrine, dipyridamole, hydralazine, amonafide, PSK (krestin), DPPE (tesmillifene), homoharringtonine, quinamed, NOV-002, or ABT-737. These drugs could serve as chemopotentiators. All agents listed in FIG. 11 are compatible with the encapsulation technologies described herein. An alternative active targeting ligand could be folate since the folate receptor is overexpressed in lung cancer. Folate can be conjugated as described in references 97, 109 and 110, which are incorporated herein as if fully set forth.

Figure 12:
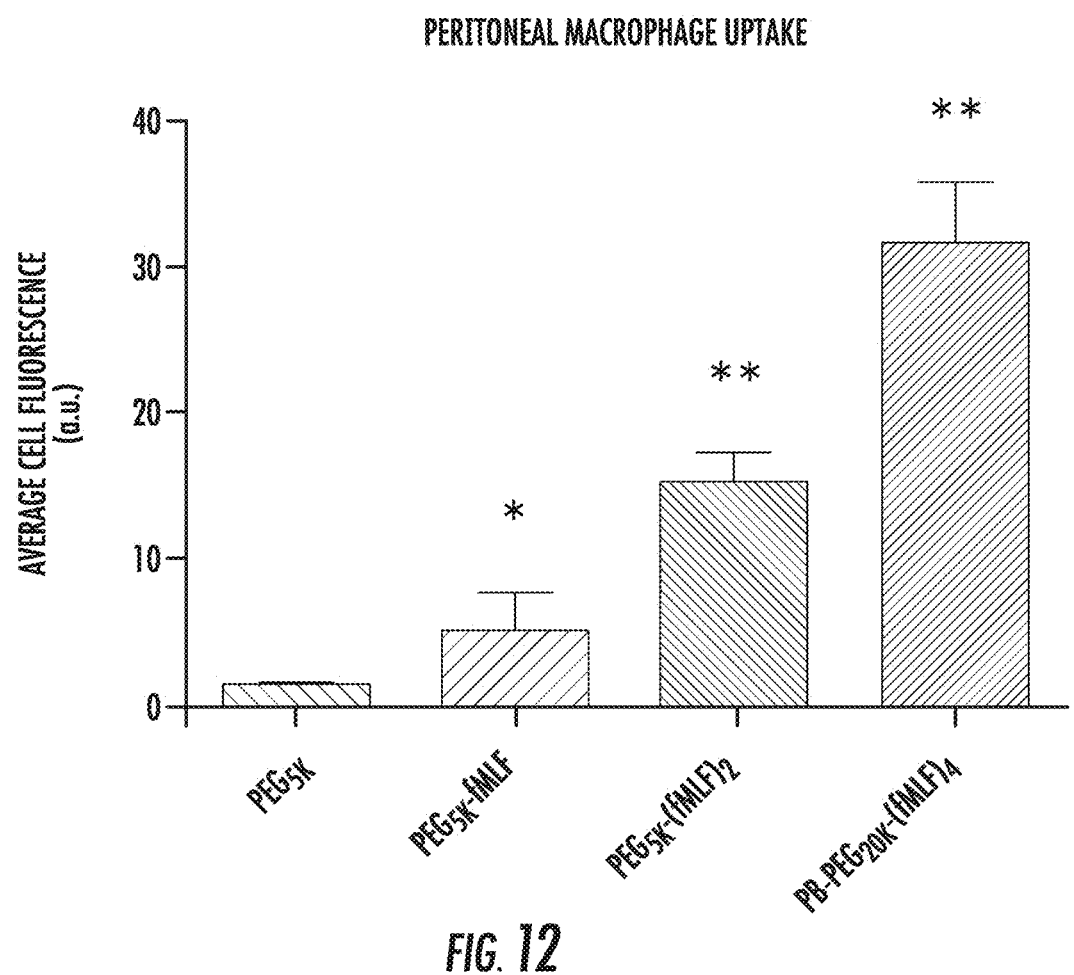
FIG. 12 illustrates uptake of PEG-fMLF nanocarriers in mouse peritoneal macrophages at 37° C. after 4 h of incubation. Means±SD for three experiments are shown for each value. (*Statistically significant difference between the control PEG5K and PEG-fMLF nanocarriers. $P<0.05$, **$P<0.01$).

Nanocarriers with multiple ligand copies improve cell targeting and control cell disposition. Changes in avidity may be considered to improve the active targeting of nanocarriers to cell surface receptors. Peptide (FIG. 12) and nonpeptide ligands (e.g., folate (see references 96, 97 and 111, which are incorporated by reference as if fully set forth) and mannose—not shown) have been conjugated on a variety of nanoconstructs. The relationship between ligand copy number, targeting activity, pharmacokinetics and cellular disposition may be considered in designing nanoconstructs of embodiments herein. The nanocarrier may be internalized or remain on the cell surface depending on the size of the nanocarrier and the number and spacing of targeting ligands as well as flexibility of the ligand linker. As seen in FIG. 12, the nonfunctionalized nanocarrier was not taken up into peritoneal macrophages in vivo. The addition of one copy of the ligand (fMLF) slightly improves interactions with the formyl peptide receptor. As copy number increase even large nanocarriers are taken up in vivo nearly 20× more than nonfunctionalized nanocarriers. Nanocarriers can be engineered to tightly bind and remain on cell surfaces (see reference 112, which is incorporated by reference as if fully set forth). Controlling ligand copy number, spacing and the flexibility of the ligand linker may enable the tuning of NP cellular disposition kinetics. For Example 2, the goal was to promote cell uptake; therefore the ligand density could be relatively low.

SELECTED REFERENCES CITED

1. Evans R. The steroid and thyroid hormone receptor superfamily. *Science.* May 13, 1988 1988; 240(4854):889-895.
2. Committee NRN. A Unified Nomenclature System for the Nuclear Receptor Superfamily. *Cell.* 1999; 97(2):161-163.
3. Olefsky J M. Nuclear Receptor Minireview Series. *Journal of Biological Chemistry.* 2001; 276(40):36863-36864.
4. Aranda A, Pascual A. Nuclear Hormone Receptors and Gene Expression. *Physiol. Rev.* Jul. 1, 2001 2001; 81(3): 1269-1304.
5. Benoit Gr, Cooney A, Giguere V, et al. International Union of Pharmacology. LXVI. Orphan Nuclear Receptors. *Pharmacological Reviews.* 2006; 58(4):798-836.
6. Bjornstrom L, Sjoberg M. Estrogen receptor-dependent activation of AP-1 via non-genomic signalling. *Nuclear Receptor.* 2004; 2(1):3.
7. Brzozowski A M, Pike A C W, Dauter Z, et al. Molecular basis of agonism and antagonism in the oestrogen receptor. *Nature.* 1997; 389(6652):753-758.
8. Busch B B, Stevens W C, Martin R, et al. Identification of a Selective Inverse Agonist for the Orphan Nuclear Receptor Estrogen-Related Receptor Œ±. *Journal of Medicinal Chemistry.* 2004; 47(23):5593-5596.
9. ESCRIVA H, LANGLOIS M-C, MENDON<<A R L, PIERCE R, LAUDET V. Evolution and Diversification of the Nuclear Receptor Superfamily<sup>a</sup>. *Annals of the New York Academy of Sciences.* 1998; 839(TRENDS IN COMPARATIVE ENDOCRINOLOGY AND NEUROBIOLOGY: FROM MOLECULAR TO INTEGRATIVE BIOLOGY):143-146.
10. Glass C K, Rosenfeld M G. The coregulator exchange in transcriptional functions of nuclear receptors. *Genes & Development.* 2000; 14(2):121-141.
11. Gronemeyer H, Gustafsson J-A, Laudet V. Principles for modulation of the nuclear receptor superfamily. *Nat Rev Drug Discov.* 2004; 3(11):950-964.
12. Heinzel N N T. Nuclear Receptors: Overview and Classification *Current Drug Targets—Inflammation & Allergy.* 2004; 3(4):335-346.
13. Klinge C M. Estrogen receptor interaction with co-activators and co-repressors[small star, filled]. *Steroids.* 2000; 65(5):227-251.
14. Klinge C M, Bodenner D L, Desai D, Niles R M, Traish A M. Binding of type II nuclear receptors and estrogen receptor to full and half-site estrogen response elements in vitro. *Nucleic Acids Research.* 1997; 25(10):1903-1912.
15. Kumar R, Thompson E B. The structure of the nuclear hormone receptors. *Steroids.* 1999; 64(5):310-319.
16. Laudet V. Evolution of the nuclear receptor superfamily: early diversification from an ancestral orphan receptor. *J Mol Endocrinol.* Dec. 1, 1997 1997; 19(3):207-226.
17. Linja M J, Porkka K P, Kang Z, et al. Expression of Androgen Receptor Coregulators in Prostate Cancer. *Clinical Cancer Research.* 2004; 10(3):1032-1040.
18. Mangelsdorf D J, Thummel C, Beato M, et al. The nuclear receptor superfamily: The second decade. *Cell.* 1995; 83(6):835-839.
19. Novac N, Heinzel T. Nuclear Receptors: Overview and Classification. *Current Drug Targets—Inflammation & Allergy.* 2004; 3(4):335-346.
20. Overington J P, Al-Lazikani B, Hopkins A L. How many drug targets are there? *Nat Rev Drug Discov.* 2006; 5(12): 993-996.
21. Pascual G, Glass C K. Nuclear receptors versus inflammation: mechanisms of transrepression. *Trends in Endocrinology & Metabolism.* 2006; 17(8):321-327.
22. Shiau A K, Barstad D, Loria P M, et al. The Structural Basis of Estrogen Receptor/Coactivator Recognition and the Antagonism of This Interaction by Tamoxifen. *Cell.* 1998; 95(7):927-937.
23. Sluder A E, Maina C V. Nuclear receptors in nematodes: themes and variations. *Trends in Genetics.* 2001; 17(4): 206-213.
24. Smith C L, O'Malley B W. Coregulator Function: A Key to Understanding Tissue Specificity of Selective Receptor Modulators. *Endocr Rev.* Feb. 1, 2004 2004; 25(1):45-71.
25. Tata J R. One hundred years of hormones. *EMBO reports.* 2005; 6(6):490-496.
26. Warnmark A, Treuter E, Wright A P H, Gustafsson J-A. Activation Functions 1 and 2 of Nuclear Receptors: Molecular Strategies for Transcriptional Activation. *Mol Endocrinol.* Oct. 1, 2003 2003; 17(10):1901-1909.
27. Wortham M, Czerwinski M, He L, Parkinson A, Wan Y-J Y. Expression of Constitutive Androstane Receptor, Hepatic Nuclear Factor 4Œ±, and P450 Oxidoreductase Genes Determines Interindividual Variability in Basal Expression and Activity of a Broad Scope of Xenobiotic Metabolism Genes in the Human Liver. *Drug Metabolism and Disposition.* 2007; 35(9):1700-1710.
28. Wu W, Niles E, Hirai H, LoVerde P. Evolution of a novel subfamily of nuclear receptors with members that each contain two DNA binding domains. *BMC Evolutionary Biology.* 2007; 7(1):27.
29. Wu W, Niles E G, El-Sayed N, Berriman M, LoVerde P T. Schistosoma mansoni (Platyhelminthes, Trematoda) nuclear receptors: Sixteen new members and a novel subfamily. *Gene.* 2006; 366(2):303-315.
30. Zhang Z, Burch P E, Cooney A J, et al. Genomic Analysis of the Nuclear Receptor Family New Insights Into Structure, Regulation, and Evolution From the Rat Genome. *Genome Research.* 2004; 14(4):580-590.
31. Zivadinovic D, Gametchu B, Watson C. Membrane estrogen receptor-alpha levels in MCF-7 breast cancer cells predict cAMP and proliferation responses. *Breast Cancer Res.* 2005; 7(1):R101-R112.
32. Mohan R, Heyman R A. Orphan Nuclear Receptor Modulators. *Current Topics in Medicinal Chemistry.* 2003; 3(14):1637-1647.
33. Akbulut M, Ginart P, Gindy M E, et al. Generic Method of Preparing Multifunctional Fluorescent Nanoparticles Using Flash NanoPrecipitation. *Advanced Functional Materials.* March 2009; 19(5):718-725.
34. Johnson B K, Prud'homme R K. Mechanism for rapid self-assembly of block copolymer nanoparticles. *Physical Review Letters.* Sep. 12 2003; 91(11).

35. Johnson B K, Prud'homme R K. Flash NanoPrecipitation of organic actives and block copolymers using a confined impinging jets mixer. *Australian Journal of Chemistry.* 2003; 56(10):1021-1024.

36. Welch C F, Rose G D, Malotky D, Eckersley S T. Rheology of high internal phase emulsions. *Langmuir.* February 2006; 22(4):1544-1550.

37. Vladisavljevic G T, Tesch S, Schubert H. Preparation of water-in-oil emulsions using microporous polypropylene hollow fibers: influence of some operating parameters on droplet size distribution. *Chemical Engineering and Processing.* 2002; 41(3):231-238.

38. Vladisavljevic G T, Kobayashi I, Nakajima M, Williams R A, Shimizu M, Nakashima T. Shirasu Porous Glass membrane emulsification: Characterisation of membrane structure by high-resolution X-ray microtomography and microscopic observation of droplet formation in real time. *Journal of Membrane Science.* September 2007; 302(1-2): 243-253.

39. Chao P Y, Deshmukh M, Kutscher H L, et al. Pulmonary targeting microparticulate camptothecin delivery system: anticancer evaluation in a rat orthotopic lung cancer model. *Anti-Cancer Drugs.* January 2010; 21(1):65-76.

40. Davis M A, Taube R A. Pulmonary Perfusion Imaging: Acute Toxicity and Safety Factors as a Function of Particle Size. *J Nucl Med.* Nov. 1, 1978 1978; 19(11): 1209-1213.

41. Schroeder H G, Bivins B A, Sherman G P, DeLuca P P. Physiological effects of subvisible microspheres administered intravenously to beagle dogs. *J Pharm Sci.* April 1978; 67(4):508-513.

42. Chiu D T, Lorenz R M. Chemistry and Biology in Femtoliter and Picoliter Volume Droplets. *Accounts of Chemical Research.* 2009; 42(5):649-658.

43. Chayen N E, Saridakis E. Protein crystallization: from purified protein to diffraction-quality crystal. *Nature Methods.* February 2008; 5(2):147-153.

44. Panagiotou T, Mesite S V, Fisher R J. Production of Norfloxacin Nanosuspensions Using Microfluidics Reaction Technology through Solvent/Antisolvent Crystallization. *Industrial & Engineering Chemistry Research.* February 2009; 48(4):1761-1771.

45. Sauter C, Dhouib K, Lorber B. From macrofluidics to microfluidics for the crystallization of biological macromolecules. *Crystal Growth & Design.* November 2007; 7(11):2247-2250.

46. Selimovic S, Jia Y W, Fraden S. Measuring the Nucleation Rate of Lysozyme using Microfluidics. *Crystal Growth & Design.* April 2009; 9(4):1806-1810.

47. Edd J F, Di Carlo D, Humphry K J, et al. Controlled encapsulation of single-cells into monodisperse picoliter drops. *Lab on a Chip.* August 2008; 8(8):1262-1264.

48. Kang L F, Chung B G, Langer R, Khademhosseini A. Microfluidics for drug discovery and development: From target selection to product lifecycle management. *Drug Discovery Today.* January 2008; 13(1-2):1-13.

49. Kline T R, Runyon M K, Pothiawala M, Ismagilov R F. ABO, D blood typing and subtyping using plug-based microfluidics. *Analytical Chemistry.* August 2008; 80(16): 6190-6197.

50. Modak N, Datta A, Ganguly R. Cell separation in a microfluidic channel using magnetic microspheres. *Microfluidics and Nanofluidics.* May 2009; 6(5):647-660.

51. Srisa-Art M, Dyson E C, Demello A J, Edel J B. Monitoring of real-time streptavidin-biotin binding kinetics using droplet microfluidics. *Analytical Chemistry.* September 2008; 80(18):7063-7067.

52. Chu L Y, Utada A S, Shah R K, Kim J W, Weitz D A. Controllable monodisperse multiple emulsions. *Angewandte Chemie-International Edition.* 2007; 46(47): 8970-8974.

53. Anna S L, Bontoux N, Stone H A. Formation of dispersions using "flow focusing" in microchannels. *Applied Physics Letters.* January 2003; 82(3):364-366.

54. Carroll N J, Rathod S B, Derbins E, Mendez S, Weitz D A, Petsev D N. Droplet-based microfluidics for emulsion and solvent evaporation synthesis of monodisperse mesoporous silica microspheres. *Langmuir.* February 2008; 24(3): 658-661.

55. Luo J K, Fu Y Q, Li Y, et al. Moving-part-free microfluidic systems for lab-on-a-chip. *Journal of Micromechanics and Microengineering.* May 2009; 19(5).

56. Nie Z H, Seo M S, Xu S Q, et al. Emulsification in a microfluidic flow-focusing device: effect of the viscosities of the liquids. *Microfluidics and Nanofluidics.* November 2008; 5(5):585-594.

57. Stone H A, Kim S. Microfluidics: Basic issues, applications, and challenges. *Aiche Journal.* June 2001; 47(6): 1250-1254.

58. Stone H A, Stroock A D, Ajdari A. Engineering flows in small devices: Microfluidics toward a lab-on-a-chip. *Annual Review of Fluid Mechanics.* 2004; 36:381-411.

59. Teh S Y, Lin R, Hung L H, Lee A P. Droplet microfluidics. *Lab on a Chip.* 2008; 8(2):198-220.

60. Umbanhowar P B, Prasad V, Weitz D A. Monodisperse emulsion generation via drop break off in a coflowing stream. *Langmuir.* January 2000; 16(2):347-351.

61. Heinrich G, Straube E, Helmis G. RUBBER ELASTICITY OF POLYMER NETWORKS—THEORIES. *Advances in Polymer Science.* 1988; 85:33-87.

62. Anseth K S, Bowman C N, BrannonPeppas L. Mechanical properties of hydrogels and their experimental determination. *Biomaterials.* September 1996; 17(17):1647-1657.

63. Bryant S J, Anseth K S, Lee D A, Bader D L. Crosslinking density influences the morphology of chondrocytes photoencapsulated in PEG hydrogels during the application of compressive strain. *Journal of Orthopaedic Research.* September 2004; 22(5):1143-1149.

64. Akagi Y, Matsunaga T, Shibayama M, Chung U, Sakai T. Evaluation of Topological Defects in Tetra-PEG Gels. *Macromolecules.* January 2010; 43(1):488-493.

65. Beamish J A, Zhu J M, Kottke-Marchant K, Marchant R E. The effects of monoacrylated poly(ethylene glycol) on the properties of poly(ethylene glycol) diacrylate hydrogels used for tissue engineering. *Journal of Biomedical Materials Research Part A.* February 2010; 92A(2):441-450.

66. Yin Y L, Prudhomme R K, Stanley F. Relationship between Poly(Acrylic Acid) Gel Structure and Synthesis. *Acs Symposium Series.* 1992; 480:91-113.

67. Doerschuk C M, Beyers N, Coxson H O, Wiggs B, Hogg J C. Comparison of neutrophil and capillary diameters and their relation to neutrophil sequestration in the lung. *J Appl Physiol.* June 1993; 74(6):3040-3045.

68. Downey G P, Doherty D E, Schwab B, 3rd, Elson E L, Henson P M, Worthen G S. Retention of leukocytes in capillaries: role of cell size and deformability. *J Appl Physiol.* November 1990; 69(5):1767-1778.

69. Formal M, Lekka M, Pyka-Fosciak G, et al. Erythrocyte stiffness in diabetes mellitus studied with atomic force microscope. *Clin Hemorheol Microcirc.* 2006; 35(1-2): 273-276.

70. Huang Y, Doerschuk C M, Kamm R D. Computational modeling of RBC and neutrophil transit through the pulmonary capillaries. *J Appl Physiol*. February 2001; 90(2): 545-564.
71. Wiggs B R, English D, Quinlan W M, Doyle N A, Hogg J C, Doerschuk C M. Contributions of capillary pathway size and neutrophil deformability to neutrophil transit through rabbit lungs. *J Appl Physiol*. July 1994; 77(1):463-470.
72. D'Souza A J M, Topp E M. Release from polymeric prodrugs: Linkages and their degradation. *Journal of Pharmaceutical Sciences*. August 2004; 93(8):1962-1979.
73. Budijono S J, Shan J, Yao N, et al. Synthesis of Stable Block-Copolymer-Protected NaYF4:Yb3+, Er3+ Up-Converting Phosphor Nanoparticles. *Chemistry of Materials*. 2009; 22(2):311-318.
74. Chao P, Deshmukh M, Kutscher H L, et al. Pulmonary targeting microparticulate camptothecin delivery system: anticancer evaluation in a rat orthotopic lung cancer model. *Anti-Cancer Drugs*. 2010; 21(1):65-76 10.1097/CAD.1090b1013e328332a328322.
75. Mathieu A, Remmelink M, D'Haene N, et al. Development of a chemoresistant orthotopic human nonsmall cell lung carcinoma model in nude mice—Analyses of tumor heterogeneity in relation to the immunohistochemical levels of expression of cyclooxygenase-2, ornithine decarboxylase, lung-related resistance protein, prostaglandin E synthetase, and glutathione-S-transferase (GST)-alpha, GST-mu, and GST-pi. *Cancer*. October 2004; 101(8): 1908-1918.
76. Onn A, Isobe T, Itasaka S, et al. Development of an orthotopic model to study the biology and therapy of primary human lung cancer in nude mice. *Clinical Cancer Research*. November 2003; 9(15):5532-5539.
77. Sunil V R, Laumbach R J, Patel K J, et al. Pulmonary effects of inhaled limonene ozone reaction products in elderly rats. *Toxicology and Applied Pharmacology*. July 2007; 222(2):211-220.
78. Sunil V R, Patel K J, Mainelis G, et al. Pulmonary effects of inhaled diesel exhaust in aged mice. *Toxicology and Applied Pharmacology*. December 2009; 241(3):283-293.
79. Fakhrzadeh L, Laskin J D, Laskin D L. Regulation of caveolin-1 expression, nitric oxide production and tissue injury by tumor necrosis factor-alpha following ozone inhalation. *Toxicology and Applied Pharmacology*. March 2008; 227(3):380-389.
80. Ungun B, Prud'homme R K, Budijono S J, et al. Nanofabricated upconversion nanoparticles for photodynamic therapy. *Optics Express*. January 2009; 17(1):80-86.
81. Wolfson T. Composite nanoparticles for MRI imaging. *Senior Thesis Princeton University*. 2008.
82. Ansell S M, Johnstone S A, Tardi P G, et al. Modulating the therapeutic activity of nanoparticle delivered paclitaxel by manipulating the hydrophobicity of prodrug conjugates. *Journal of Medicinal Chemistry*. June 2008; 51(11): 3288-3296.
83. Cheng Y, Prud'homme R K, Thomas J L. Diffusion of mesoscopic probes in aqueous polymer solutions measured by fluorescence recovery after photobleaching. *Macromolecules*. Oct. 8 2002; 35(21):8111-8121.
84. Haggerty L, Sugarman J H, Prudhomme R K. Diffusion of Polymers through Polyacrylamide Gels. *Polymer*. June 1988; 29(6):1058-1063.
85. Gindy M E, Ji S X, Hoye T R, Panagiotopoulos A Z, Prud'homme R K. Preparation of Poly(ethylene glycol) Protected Nanoparticles with Variable Bioconjugate Ligand Density. *Biomacromolecules*. October 2008; 9(10): 2705-2711.
86. Deshmukh M, Chao P, Kutscher H L, Gao D, Sinko P J. A Series of ɶ±-Amino Acid Ester Prodrugs of Camptothecin: In Vitro Hydrolysis and A549 Human Lung Carcinoma Cell Cytotoxicity. *Journal of Medicinal Chemistry*. 2010; 53(3):1038-1047.
87. Dharap S S, Qiu B, Williams G C, Sinko P, Stein S, Minko T. Molecular targeting of drug delivery systems to ovarian cancer by BH3 and LHRH peptides. *Journal of Controlled Release*. August 2003; 91(1-2):61-73.
88. Dharap S S, Wang Y, Chandna P, et al. Tumor-specific targeting of an anticancer drug delivery system by LHRH peptide. *Proceedings of the National Academy of Sciences of the United States of America*. September 2005; 102(36): 12962-12967.
89. Gupta E, Cook T J, Rubin E H, Sinko P J. Characterization and in vitro in vivo correlation of the intestinal permeability of 20(S) camptothecin (CPT). *Faseb Journal*. February 1997; 11(3):1737-1737.
90. Gupta E, Luo F, Lallo A, et al. The intestinal absorption of camptothecin, a highly lipophilic drug, across Caco-2 cells is mediated by active transporter(s). *Anticancer Research*. March-April 2000; 20(2A):1013-1016.
91. Gupta E, Vyas V, Ahmed F, Sinko P, Cook T, Rubin E. Pharmacokinetics of orally administered camptothecins. In: Liehr J G, Giovanella B C, Verschaegen C F, eds. *Camptothecins: Unfolding Their Anticancer Potential*. Vol 9222000:195-204.
92. Luo F R, Paranjpe P V, Guo A, Rubin E, Sinko P. Intestinal transport of irinotecan in Caco-2 cells and MDCK II cells overexpressing efflux transporters PGP, cMOAT, and MRP1. *Drug Metabolism and Disposition*. July 2002; 30(7):763-770.
93. Lalloo A, Chao P, Hu P, Stein S, Sinko P J. Pharmacokinetic and pharmacodynamic evaluation of a novel in situ forming poly(ethylene glycol)-based hydrogel for the controlled delivery of the camptothecins. *Journal of Controlled Release*. May 2006; 112(3):333-342.
94. Lalloo A K, Luo F R, Guo A, et al. Membrane transport of camptothecin: Facilitation by human P-glycoprotein (ABCB1) and multidrug resistance protein 2 (ABCC2). *BMC Medicine*. 2004; 2.
95. Minko T, Paranjpe P V, Qiu B, et al. Enhancing the anticancer efficacy of camptothecin using biotinylated poly(ethyleneglycol) conjugates in sensitive and multidrug-resistant human ovarian carcinoma cells. *Cancer Chemotherapy and Pharmacology*. August 2002; 50(2): 143-150.
96. Paranjpe P V, Chen Y, Kholodovych V, Welsh W, Stein S, Sinka P J. Tumor-targeted bioconjugate based delivery of camptothecin: design, synthesis and in vitro evaluation. *Journal of Controlled Release*. November 2004; 100(2): 275-292.
97. Paranjpe P V, Stein S, Sinko P J. Tumor-targeted and activated bioconjugates for improved camptothecin delivery. *Anti-Cancer Drugs*. 2005; 16(7):763-775.
98. Rajendra R, Gounder M K, Saleem A, et al. Differential effects of the breast cancer resistance protein on the cellular accumulation and cytotoxicity of 9-aminocamptothecin and 9-nitrocamptothecin. *Cancer Research*. June 2003; 63(12):3228-3233.
99. Su Y M, Zhang X P, Sinko P J. Exploitation of drug-induced Bcl-2 overexpression for restoring normal apoptosis function: A promising new approach to the treatment of multidrug resistant cancer. *Cancer Letters*. August 2007; 253(1):115-123.

100. Lee E S, Na K, Bae Y H. Polymeric micelle for tumor pH and folate-mediated targeting. *J Control Release*. Aug. 28 2003; 91(1-2):103-113.

101. Schanker L S, Less M J. Lung pH and pulmonary absorption of nonvolatile drugs in the rat. *Drug Metab Dispos*. March-April 1977; 5(2):174-178.

102. Chou T C. Theoretical basis, experimental design, and computerized simulation of synergism and antagonism in drug combination studies. *Pharmacological Reviews*. September 2006; 58(3):621-681.

103. Chou T C. Preclinical versus clinical drug combination studies. *Leukemia & Lymphoma.* 2008; 49(11):2059-2080.

104. Chou T C, Talalay P. QUANTITATIVE-ANALYSIS OF DOSE-EFFECT RELATIONSHIPS—THE COMBINED EFFECTS OF MULTIPLE-DRUGS OR ENZYME-INHIBITORS. *Advances in Enzyme Regulation.* 1984; 22:27-55.

105. Chou T-C. Theoretical Basis, Experimental Design, and Computerized Simulation of Synergism and Antagonism in Drug Combination Studies. *Pharmacological Reviews.* 2006; 58(3):621-681.

106. Chou T-C. Preclinical versus clinical drug combination studies. *Leukemia & Lymphoma.* 2008; 49(11):2059-2080.

107. Chou T-C, Talalay P. Quantitative analysis of dose-effect relationships: the combined effects of multiple drugs or enzyme inhibitors. *Advances in Enzyme Regulation.* 1984; 22:27-55.

108. Mazzio E A, Soliman K F. Effects of enhancing mitochondrial oxidative phosphorylation with reducing equivalents and ubiquinone on 1-methyl-4-phenylpyridinium toxicity and complex I-IV damage in neuroblastoma cells. *Biochem Pharmacol*. Mar. 15 2004; 67(6):1167-1184.

109. Vortherms A R, Doyle R P, Gao D, Debrah O, Sinko P J. Synthesis, Characterization, and In Vitro Assay of Folic Acid Conjugates of 3,Äs-Azido-3,Äs-Deoxythymidine (AZT): Toward Targeted AZT Based Anticancer Therapeutics. *Nucleosides, Nucleotides and Nucleic Acids.* 2008; 27(2):173-185.

110. Paranjpe P V, Chen Y, Kholodovych V, Welsh W, Stein S, Sinko P J. Tumor-targeted bioconjugate based delivery of camptothecin: design, synthesis and in vitro evaluation. *Journal of Controlled Release.* 2004; 100(2):275-292.

111. Vortherms A R, Doyle R P, Gao D, Debrah O, Sinko P J. Synthesis, characterization, and in vitro assay of folic acid conjugates of 3'-azido-3'-deoxythymidine (AZT): Toward targeted AZT based anticancer therapeutics. *Nucleosides Nucleotides & Nucleic Acids.* 2008; 27(2): 173-185.

112. Wan L, Zhang X, Gunaseelan S, et al. Novel multicomponent nanopharmaceuticals derived from poly(ethylene) glycol, retro-inverso-Tat nonapeptide and saquinavir demonstrate combined anti-HIV effects. *AIDS Research and Therapy.* 2006; 3(1).

113. Goodrich, K., A. Yoshimura, et al. Measurement of the Modulus and Yield Strength of Soft Gels—Experiments and Numerical-Simulation (1989) Journal of Rheology 33(2): 317-327.

The references cited throughout this application, are incorporated herein for all purposes apparent in this application and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A delivery system comprising a gel microparticle, a plurality of nanoparticles associated with the gel microparticle, and one or more hydrophobic drugs associated with at least one of the nanoparticles, wherein the gel microparticle includes aqueous soluble polymers or copolymers that are gelled by a crosslinking reaction selected from the group consisting of free radical polymerization, mannich reactions, hydrophobic association, metal ion mediated complexation, amide formation reactions, ester formation reactions, and azide alkyne Huisgen cycloaddition, and the nanoparticles include PEG protective coatings.

2. The delivery system of claim 1 further comprising at least one of one or more targeting agents associated with at least one of the nanoparticles or one or more chemopotentiator associated with at least one of the nanoparticles.

3. The delivery system of claim 1, wherein the gel microparticles include polymers and degradable linkages between individual ones of the polymers.

4. The delivery system of claim 1, wherein the gel microparticles have a size of 1-60 μm.

5. The delivery system of claim 1, wherein the gel microparticles have a size selected from the group consisting of 6-10 μm and 50-60 μm.

6. The delivery system of claim 1, wherein the shear modulus of the gel microparticle is from 4 Pa to 200,000 Pa.

7. The delivery system of claim 1, wherein the gel microparticle includes gelled polymers or copolymers selected from at least one of poly(2-hydroxyethyl methacrylate), polyphosphate, polyethylene glycol, PEG, or copolymers thereof, dextran, polyvinyl pyrrolidone or co-polymers thereof, or polyacrylic acid or copolymers thereof.

8. The delivery system of claim 1, wherein the gel microparticle includes gelled polymers or copolymers selected from at least one of polyethylene glycol, PEG, having a molecular weight from 200 to 200,000 g/mole, dextran having a molecular weight from 200 to 100,000 g/mole, polyvinyl pyrrolidone or copolymers thereof having a molecular weight from 200 to 100,000 g/mole, or polylactic acid-polyethylene glycol-polylactic acid, PLA-PEG-PLA, polymers.

9. The delivery system claim 1, wherein the one or more hydrophobic drugs includes a substance selected from the group consisting of an asthma therapeutic agent, a chronic obstructive pulmonary disease therapeutic agent, a tuberculosis therapeutic agent, a cancer therapeutic agent, a non-small cell lung cancer therapeutic agent, signal transduction inhibitors, cytotoxic agents, cell cycle inhibitors, cell cycle control inhibitors, checkpoint inhibitors that interfere with the normal function of cell cycle checkpoints, checkpoint inhibitors that interfere with the normal function of cell cycle S/G2 checkpoint, checkpoint inhibitors that interfere with the normal function of cell cycle G2/M checkpoint, checkpoint inhibitors that interfere with the normal function of cell cycle G1/S checkpoint, topoisomerase inhibitors, camptothecins, enzymes necessary for DNA replication, enzymes necessary for DNA transcription, receptor tyrosine kinase inhibitors, apoptosis inducing agents, antimetabolites, gemcitabine, hydroxyurea, telomerase inhibitors, cyclin-dependent kinase inhibitors, cytoskeletal proteins, transcription factors, tumor suppresser genes, DNA damaging agents, DNA repair inhibitors, anti-angiogenic agents, mitochondrial poisons, carboplatin, cisplatin, cyclophosphamide, doxorubicin, daunorubicin, epirubicin, mitomycin C, mitoxantrone, 5-fluorouracil (5-FU), FUDR, methotrexate, topoisomerase I inhibitors, irinotecan, topotecan, S/G2 checkpoint inhibitors, bleomycin, docetaxel, etoposide, paclitaxel, vinblastine, vincristine, vindesine, vinorelbine, genistein, trastuzumab, ZD1839, apoptosis-inducing agents, a TB therapeutic agent, ethambutol, isoniazid, pyrazinamide, rifampicin, streptomycin, aminoglycosides, amikacin (AMK), kanamycin (KM), polypeptides, capreomycin, viomycin, enviomycin, fluoroquinolones, ciprofloxacin (CIP), levofloxacin, moxifloxacin (MXF), thioamides, ethionamide, prothionamide, cycloserine, p-aminosalicylic acid (PAS or P), rifabutin, macrolides, clarithromycin (CLR), linezolid (LZD), thioacetazone (T), thioridazine, arginine, vitamin D, R207910, SQ641, a COPD therapeutic agent, short-acting selective $beta_2$-adrenoceptor agonists, adrenergic agonists, anticholinergic medications and long-acting $\beta_2$-agonists, or a pharmaceutically acceptable salt of one of the foregoing.

10. The delivery system of claim 1 further comprising a pharmaceutically acceptable carrier.

11. A method of treating a condition comprising administering a delivery system to a patient in need thereof, the delivery system including a gel microparticle, a plurality of nanoparticles associated with the gel microparticle, and one or more hydrophobic drugs associated with at least one of the nanoparticles, wherein the gel microparticle includes aqueous soluble polymers or copolymers that are gelled by a crosslinking reaction selected from the group consisting of free radical polymerization, mannich reactions, hydrophobic association, metal ion mediated complexation, amide formation reactions, ester formation reactions, and azide alkyne Huisgen cycloaddition, and the nanoparticles include PEG protective coatings.

12. The method of claim 11, wherein the step of administering includes intravenous injection.

13. The method of claim 11, wherein the step of administering includes intra-arterial injection.

14. The method of claim 11, wherein the delivery system further includes at least one of one or more targeting agents associated with the nanoparticles or one or more chemopotentiators associated with the nanoparticles.

15. The method of claim 11, wherein the gel microparticles include polymers and degradable linkages between individual ones of the polymers.

16. The method of claim 11, wherein the gel microparticles have a size of 1-60 μm.

17. The method of claim 11, wherein the gel microparticles have a size selected from the group consisting of 6-10 μm and 50-60 μm.

18. The method of claim 11, wherein the one or more hydrophobic drugs includes a substance selected from the group consisting of an asthma therapeutic agent, a chronic obstructive pulmonary disease therapeutic agent, a tuberculosis therapeutic agent, a cancer therapeutic agent, a non-small cell lung cancer therapeutic agent, signal transduction inhibitors, cytotoxic agents, cell cycle inhibitors, cell cycle control inhibitors, checkpoint inhibitors that interfere with the normal function of cell cycle checkpoints, checkpoint inhibitors that interfere with the normal function of cell cycle S/G2 checkpoint, checkpoint inhibitors that interfere with the normal function of cell cycle G2/M checkpoint, checkpoint inhibitors that interfere with the normal function of cell cycle G1/S checkpoint, topoisomerase inhibitors, camptothecins, enzymes necessary for DNA replication, enzymes necessary for DNA transcription, receptor tyrosine kinase inhibitors, apoptosis inducing agents, antimetabolites, gemcitabine, hydroxyurea, telomerase inhibitors, cyclin-dependent kinase inhibitors, cytoskeletal proteins, transcription factors, tumor suppresser genes, DNA damaging agents, DNA repair inhibitors, anti-angiogenic agents, mitochondrial poisons, carboplatin, cisplatin, cyclophosphamide, doxorubicin, daunorubicin, epirubicin, mitomycin C, mitoxantrone, 5-fluorouracil (5-FU), FUDR, methotrexate, topoisomerase I inhibitors, irinotecan, topotecan, S/G2 checkpoint inhibitors, G2/M checkpoint inhibitors, bleomycin, docetaxel, etoposide, paclitaxel, vinblastine, vincristine, vindesine, vinorelbine, G1/early-S checkpoint inhibitors, genistein, trastuzumab, ZD1839, apoptosis-inducing agents, a TB therapeutic agent, ethambutol, isoniazid, pyrazinamide, rifampicin, streptomycin, aminoglycosides, amikacin (AMK), kanamycin (KM), polypeptides, capreomycin, viomycin, enviomycin, fluoroquinolones, ciprofloxacin (CIP), levofloxacin, moxifloxacin (MXF), thioamides, ethionamide, prothionamide, cycloserine, p-aminosalicylic acid (PAS or P), rifabutin, macrolides, clarithromycin (CLR), linezolid (LZD), thioacetazone (T), thioridazine, arginine, vitamin D, R207910, SQ641, a COPD therapeutic agent, short-acting, selective $beta_2$-adrenoceptor agonists, adrenergic agonists, anticholinergic medications and long-acting $\beta_2$-agonists, or a pharmaceutically acceptable salt of one of the foregoing.

19. The method of claim 11, wherein the delivery system further includes a pharmaceutically acceptable carrier.

20. The delivery system of claim 1, wherein the one or more hydrophobic drugs include at least one hydrophobic drug selected from camptothecin, gemcitabine, carboplatin, cisplatin, doxorubicin, daunorubicin, topotecan, bleomycin, docetaxel, or paclitaxel.

21. The delivery system of claim 1, wherein the one or more hydrophobic drugs include at least one hydrophobic drug selected from ethambutol, isoniazid, pyrazinamide, rifampicin, or streptomycin.

22. The delivery system of claim 1, wherein the one or more hydrophobic drugs include camptothecin.

23. The delivery system of claim 1, wherein the one or more hydrophobic drugs include rifampicin.

24. The delivery system of claim 1, wherein the aqueous soluble polymers or copolymers include PEG polymers having a molecular weight of 200 to 200,000 g/mole.

25. The delivery system of claim 1, wherein the aqueous soluble polymers or copolymers are PEG polymers having a molecular weight of 200 to 200,000 g/mole and the one or more hydrophobic drugs include camptothecin.

26. The delivery system of claim 1, wherein the aqueous soluble polymers or copolymers are PEG polymers having a molecular weight of 200 to 200,000 g/mole and the one or more drugs include rifampicin.

27. The method of claim 11, wherein the one or more hydrophobic drugs include at least one hydrophobic drug selected from camptothecin, gemcitabine, carboplatin, cisplatin, doxorubicin, daunorubicin, topotecan, bleomycin, docetaxel, or paclitaxel.

28. The method of claim 11, wherein the one or more hydrophobic drugs include at least one hydrophobic drug selected from ethambutol, isoniazid, pyrazinamide, rifampicin, or streptomycin.

29. The method of claim 11, wherein the one or more hydrophobic drugs include camptothecin.

30. The method of claim 11, wherein the one or more hydrophobic drugs include rifampicin.

31. The method of claim 11, wherein the aqueous soluble polymers or copolymers include PEG polymers having a molecular weight of 200 to 200,000 g/mole.

32. The method of claim 11, wherein the aqueous soluble polymers or copolymers are PEG polymers having a molecular weight of 200 to 200,000 g/mole and the one or more hydrophobic drugs include camptothecin.

33. The method of claim 11, wherein the aqueous soluble polymers or copolymers are PEG polymers having a molecular weight of 200 to 200,000 g/mole and the one or more hydrophobic drugs include rifampicin.

\* \* \* \* \*